(12) United States Patent
Ramachandran et al.

(10) Patent No.: US 7,087,226 B2
(45) Date of Patent: Aug. 8, 2006

(54) LYSIN-DEFICIENT BACTERIOPHAGES HAVING REDUCED IMMUNOGENICITY

(75) Inventors: Janakiraman Ramachandran, Palo Alto, CA (US); Sriram Padmanabhan, Bangalore (IN); Bharathi Sriram, Bangalore (IN)

(73) Assignee: Gangagen, Inc., Palo Alto, CA (US)

( * ) Notice: Subject to any disclaimer, the term of this patent is extended or adjusted under 35 U.S.C. 154(b) by 0 days.

(21) Appl. No.: 11/053,982

(22) Filed: Feb. 8, 2005

(65) Prior Publication Data

US 2005/0226851 A1 Oct. 13, 2005

Related U.S. Application Data

(63) Continuation of application No. 10/259,197, filed on Sep. 27, 2002, now Pat. No. 6,896,882.

(60) Provisional application No. 60/325,803, filed on Sep. 27, 2001.

(51) Int. Cl.
*A01N 63/00* (2006.01)

(52) U.S. Cl. .................. 424/93.2; 424/93.1; 424/93.3; 424/93.6; 435/5; 435/235.1

(58) Field of Classification Search .................... 435/5, 435/235.1; 424/93.1, 93.2, 93.3, 93.6
See application file for complete search history.

(56) References Cited

U.S. PATENT DOCUMENTS

| 4,376,110 A | 3/1983 | David et al. |
|---|---|---|
| 6,056,955 A | 5/2000 | Fischetti et al. |
| 6,083,684 A | 7/2000 | Gasson |
| 6,130,082 A | 10/2000 | Majarian et al. |
| 6,395,504 B1 | 5/2002 | Trudil |
| 6,896,882 B1 | 5/2005 | Ramachandran et al. |

FOREIGN PATENT DOCUMENTS

| WO | WO 99/29342 | 6/1999 |
|---|---|---|
| WO | WO 03/026767 | 4/2003 |

OTHER PUBLICATIONS

Abul-Hassan et al., "Bacteriophage Therapy of Pseudomonas Burn Wound Sepsis," Annals of the MBC—vol. 3-n'4—Dec. 1990, pp. 1-4, Apr. 8, 2003.
Ackermann, "Tailed bacteriophages: the order caudovirales," *Adv Virus Res*, 51:135-201. (1998).
Arendt et al., Molecular Characterization of Lactorcoccal Bacteriophage Tuc2009 and Indentification and Analysis of Genes Encoding Lysin, a Putative Holin, and Two Structural Proteins, Applied and Environment Microbiology, Jun. 1994, p. 1875-1883, vol. 60, No. 6.
Auad et al., "Physical mapping and partial genetic characterization of the Lactobacillus delbrueckii subsp. bulgaricus bacteriophage lb539," *Arch Virol*, 144: 1503-1512. (1999).
Barrow et al., "Use of Lytic Bacteriophage for Control of Experimental *Escherichia coli* Septicemia and Meningitis in Chickens and Calves," Clinical and Diagnostic Laboratory Immunology, vol. 5, No. 3, pp. 294-.
Biswas, et al., "Bacteriophage Therapy Rescues Mice Bacteremic from a Clinical Isolate of Vancomycin-Resistant *Enterococcus Faecium*," Infection and Immunity, vol. 70, No. 1, pp. 204-210, Jan. 2002.
Boizet et al., "Cloning, expression and sequence analysis of an endolysin-encoding gene of Lactobacillus bulgaricus bacteriophage mv1." *Gene*, 94: 61-67 (1990).
Botstein et al., "Strategies and Applications of in Vitro Mutagenesis," Science 229, vol. 229, pp. 1193-1201, No. 4719 (1985).
Calandra et al., "Cellular streptolysin S-related hemolysins of group A Streptococcus C203S," *Infect Immun*, 12: 13-28. (1975).
Calandra et al., "Lysis and protoplast formation of group B streptococci by mutanolysin,"*Infect Immun*, 28: 1033-1037 (1980).
Caldentey et al., The Lytic Enzyme of the Pseudommonas Phage Φ6. Purification and Biochemical Characterization, Biochimica et Biophysica Acta, 1159, 44-50 (1992).
Cattozzo et al., "Expression and Immunogenicity of $V_3$ Loop Epitopes of HIV-1, Isolates SC and WMJ2, Inserted in *Salmonella Flagellin*," Journal Biotechnology 56 (1997) 191-203.
Chalfie et al., "Green Fluorescent Protein as a Marker for Gene Expression," Science, vol. 263, 802-805 1994.

(Continued)

*Primary Examiner*—Jeffrey Stucker
(74) *Attorney, Agent, or Firm*—Carol L. Francis; Bozicevic, Field & Francis LLP

(57) ABSTRACT

The present invention features therapeutic bacteriophage deficient in the lysin protein ("Lys minus" phage). Lys minus bacteriophage are incapable of facilitating efficient lysis of the bacterial host since the enzymatic activity of the lysin of the phage is needed for breaking down the peptidoglycan layer of the bacterial cell wall. Lys minus bacteriophage retain activity in invasion of its appropriate bacterial host, destruction of the bacterial genome, and replication, which are sufficient to inhibit bacterial growth and replication. Therefore, the therapeutic Lys minus phage stops the spread of infection by the bacterial pathogen without lysis of the bacterium. This approach is attractive as it also prevents the release of the phage progeny, thus reducing or eliminating the potential for generation of immune responses against the phage. The incapacitated bacterial pathogen is then removed by the normal defense systems such as phagocytes and macrophages.

33 Claims, 5 Drawing Sheets

OTHER PUBLICATIONS

Chandry et al., "Analysis of the DNA sequence, gene expression, origin of replication and modular structure of the Lactococcus lactis lytic bacteriophage sk1," *Mol Microbiol*, 26: 49-64 (1997).

Cohen et al., "Simple procedure for production by group C streptococci of phage- associated lysin active against group A streptococci," *Appl Microbiol*, 29: 175-178 (1975).

Cole et al., "The EBV-hybridoma technique and its application to human lung cancer," Monoclonal Antibodies And Cancer Therapy, Alan R. Liss, Inc., pp. 77-96 (1985).

Cote et al., "Generation of human monoclonal antibodies reactive with cellular antigens," Proc. Natl. Acad. Sci. USA 8: 2026-2030 (1983).

Coleman et al., "Cloning and expression in *Escherichia coli* and *Staphylococcus aureus* of the beta-lysin determinant from *Staphylococcus aureus*: evidence that bacteriophage conversion of beta-lysin activity is caused by insertional inactivation of the beta-lysin determinant," Microb Pathog, 1: 549-564 (1986).

Coleman et al., *Staphylococcus aureus* bacteriophages mediating the simultaneous lysogenic conversion of beta-lysin, staphylokinase and enterotoxin A: molecular mechanism of triple conversion.*J Gen Microbiol*, 135.

Cooney et al., "Molecular cloning and genetic analysis of the determinant for gamma- lysin, a two-component toxin of *Staphylococcus aureus*," *J Gen Microbiol*, 134:2179-2188 (1988).

Cormack, et al., "FACS-optimized mutants of the green fluorescent protein (GFP)," Gene, 173, 33-38 (1996).

Devine et al. "EcoRI Cleavage Sites in the argECBHRegion of the *Escherichia coli*", Chromosome H. Bacteriology, 1977. 129(2):1072-1077.

de Ruyter et al., "Food-grade controlled lysis of *Lactococcus lactis* for accelerated cheese ripening," *Nat Biotechnol*, 15: 976-979 (1997).

Diaz et al., "The two-step lysis system of pneumococcal bacteriophage EJ-1 is functional in gram-negative bacteria: triggering of the major pneumococcal autolysin in *Escherichia coli*," *Mol Microbiol*, 19: 667-681.

Dietrich et al., "Delivery of antigen-encoding plasmid DNA into the cytosol of macrophages by attenuated suicide Listeria monocytogenes," *Nat Biotechnol*, 16: 181-185 (1998).

Elias et al., "*Staphylococcus aureus haemolysins*: their use in strain typing," *Acta Microbiol Acad Sci Hung*, 27: 183-190 (1980).

Fischetti et al., "Purification and physical properties of group C streptococcal phage- associated lysine," *J Exp Med*, 133: 1105-1117 (1971).

Gaeng et al., "Gene cloning and expression and secretion of listeria monocytogenes bacteriophage-lytic enzymes in lactococcus lactis," Appl. Environ. Microbiol. 66, 2951 (2000).

Garcia et al., "Biochemical characterization of a murein hydrolase induced by bacteriophage Dp-1 in *Streptococcus pneumoniae*: comparative study between bacteriophage-associated lysin and the host amidase," *J.*

Garcia et al., "Cloning, purification, and biochemical characterization of the pneumococcal bacteriophage Cp-1 lysin," *J Virol*, 61: 2573-2580 (1987).

Garcia et al., "Mechanism of phage-induced lysis in pneumococci." J Gen Microbiol, 129: 479-487. (1983).

Garrett, "Cell Lysis by induction of cloned lambda lysis genes," J. et al. Mol. Gen. Genet. 182, 326 (1981).

Garvey et al., "Nucleotide sequence of bacillus phage Φ29 genes 14 and 15: homology of gene 15 with other phage lysozymes," Nucleic Acids Res. 14, 10001 (1986).

Gindreau et al., "Molecular analysis of the region encoding the lytic system from *Oenococcus oeni* temperate bacteriophage phi 10MC," *FEMS Microbiol Lett*, 171: 231-238 (1999).

Gründling et al. "Genetic and Biochemical Analysis of Dimer and Oligomer Interactions of theλS Holin", J. Bacteriol. Nov. 2000. 182(21):6082-6090.

Gründling et al. "Holins Kill without warning", (2001) Proc Natl Acad Sci U S A. Jul. 31, 2001:98(16):9348-52.

Henikoff, "Unidirectional digestion with exonuclease III creates targeted breakpoints for DNA sequencing," Gene 28, 351 (1984).

Henrich et al., "Primary structure and functional analysis of the lysis genes of *Lactobacillus gasseri* bacteriophage phi adh," *J Bacteriol*, 177: 723-732 (1995).

Higuchi et al., "A general method of in vitri preparation and specific mutagenesis of DNA framents: study of protein and DNA interactions," Nucleic Acids Res. 16, 7351 (1988).

Hill et al., Identification of a lysin associated with a bacteriophage (A25) virulent for group A *streptococci.J Bacteriol*, 145: 696-703 (1981).

Inouye et al., "Bacteriophage T7 lysozyme is an n-acetylmuramyl-Lalanine amidase" Biol.Chem. 248, 7247 (1973).

Jain et al., "Use of lambda phage s and r gene products in an inducible lysis system for vibrio cholerae and salmonella enterica serovar typhimurium-based DNA vaccine delivery systems," Infect Immun, 68, 986 (2000).

Jerne, "Towards a network theory of the immune system," Ann.Immunol. (Paris) 125c:373-389 (1974).

Jerne, N. K., et al., "Recurrent idiotopes and internal images," EMBO I:234 (1982).

Kaneko et al., "Complete nucleotide sequence and molecular characterization of the temperate staphylococcal bacteriophage phiPVL carrying Panton-Valentine leukocidin genes," *Gene*, 215:57-67 (1998).

Kohler et al., "Continuous cultures of fused cells secreting antibody of predefined specificity," Nature 256, 495-497 (1975).

Kosbor et al., "The production of monoclonal antibodies from human lymphocytes," Immunology Today 4, 72 (1983).

Kuhnemund, "Studies of the lysis of streptococcus pyogenes (group A, type 1) by phage-associated lysin (author's transl)" *Z Immunitatsforsch Exp Klin Immunol*, 143:184-191 (1972).

Lee et al., "Potential of bacteriophage application as an intervention strategy against Salmonella in pigs", available on the internet as of 2002 at www.extension.iastate.edu/ipic/reports/02swinereports/as1-1810.pdf.

Loessner et al., "Heterogeneous endolysins in Listerial monocytogenes bacteriophages: a new class of enzymes and evidence for conserved holin genes within the siphoviral lysis cassettes," *Mol Microbiol*, 16:1231-1241.

Loessner et al., "Modified Listeria bacteriophage lysin genes (ply) allow efficient overexpression and one-step purification of biochemically active fusion proteins," *Appl Environ Microbiol*, 62: 3057-3060 (1996).

Longchamp, et al., "Genetic control and mechanism of celi Lysis by defective bacteriophages of *Bacillas subtilis*", Abstract of the Gen. Meet. Of Amer. Soc. For Microbiol. May 19-23 p. 576. (Abstract M-16).

Martin et al. 91998) "Functional analysis of the two-gene lysis system of the pneumococcal phage Cp-1 in homologous and heterologous host cells," *J Bacteriol*, 180:210-217 (1998).

Matsuzaki et al., "Experimental Protection of Mice Against Lethal *Staphylococcus aureus* Infection by Novel Bacteriophage ø MR11," J. Infect Dis., 2003:187 (Feb. 15) pp. 613-624.

Mermod et al., "Vector for regulated expression of cloned genes in a wide range of gram-negative bacteria," J. Bacteriol. 167, 447(1986).

Mindich et al., "Cell wall lysin as a component of the bacteriophage phi 6 virion," *J. Virol*, 30: 489-496 (1979).

Mullan et al., "Lysin production by phi C2(W), a prolate phage for *Streptococcus lactis* C2," *J Dairy Res*, 52: 113-121 (1985).

Mullan et al., "Partial purification and some properties of phi C2(W) lysin, a lytic enzyme produced by phage-infected cells of *Streptococcus lactis* C2," *J Dairy Res*, 52:123-138 (1985).

Nelson et al., "Prevention and elimination of upper respiratory colonization of mice by group A streptococci by using a bacteriophage lytic enzyme," *Proc Natl Acad Sci U S A*, 98: 4107-4112 (2001).

Newton et al., "Expression and immunogenicity of an 18-residue epitope of HIV1 gp41 inserted in the flagellar protein of a salmonella live vaccine," Res. Microbiol. 146, 203-216 (1995).

Newton et al., "Immune response to cholera toxin epitope inserted in salmonella flagellin," Science 244, 70 (1989).

Norrby, E., Summary, in Vaccines 85, Lerner, R. A., R. M. Chanock, and F. Brown (eds.), Cold Spring Harbor Laboratory, Cold Spring Harbor, N.Y., pp. 388-389 (1985).

Oki et al., "Cloning, sequence analysis, and expression of the genes encoding lytic functions of Bacteriophage phi g l e," *Gene*, 176: 215-223 (1996).

Owen et al., "Nucleotide sequence of the lysozyme gene of bacteriophage T4—analysis of mutations involving repeated sequences," J. Mol. Biol. 165, 229 (1983) Schmidt et al. J. Bacteriol. 178, 1099 (1983).

Payne et al., "Exploitation of a chromosomally integrated lactose operon for controlled gene expression in *Lactococcus lactis*," FEMS Microbiol Lett, 136: 19-24 (1996).

Raina, "Purification of Streptococcus group C bacteriophage lysine," *J Bacteriol*, 145: 661-663 (1981).

Ramesh, et al., "Prevention of *Clostridium difficile*—induced ileocecitis with Bacteriophage," Anaerobe (1999) 5:69-78.

Rennell et al., "Phage P22 lysis genes: nucleotide sequences and functional relationships with T4 and 2 genes," Virol. 143, 280 (1985).

Rosenberg, et al., "Regulatory sequences involved in the promotion and termination of RNA transcription," Ann. Rev. Genet. 13, 319-53 (1979).

Stable et al., "The lysins of bacteriophages infecting lactic acid bacteria," *Appl Microbiol Biotechnol*, 43: 1-6 (1995).

Sanders et al., "A chloride-inducible gene expression cassette and its use in induced lysis of *Lactococcus lactis. Appl. Environ Microbiol*," vol. 63, No. 12, 4877-4882 (1997).

Schmidt et al., "Three functions of bacteriophage p1 involved in cell lysis," J. Bacteriol., vol. 178, No. 4, 1099-1104 (1996).

Shearman et al., "Cloning and DNA sequence analysis of a *Lactococcus* bacteriophage lysin gene," *Mol Gen Genet*, 218: 214-221 (1989).

Shearman et al., "Controlled expression and structural organization of a *Lactococcus lactis* bacteriophage lysin encoded by two overlapping genes," *Appl Environ Microbiol*, 60: 3063-3073 (1994).

Sheehan et al., "Analysis of the catalytic domain of the lysin of the lactococcal bacteriophage Tuc2009 by chimeric gene assembling." *FEMS Microbiol Lett*, 140:23-28 (1996).

Sheehan et al., "The lytic enzyme of the pneumococcal phage Dp-1: a chimeric lysin of intergeneric origin." *Mol Microbiol*, 25: 717-725 (1997).

Sheehan et al., "Identification and characterization of a lysis module present in a large proportion of bacteriophages infecting *Streptococcus thermophilus*." Appl environ Microbiol, 65: 569-577 (1999).

Shortle et al., "Gap misrepair mutagenesis: efficient site-directed induction of transition, transversion, and frameshift mutations in vitro." Proc.Natl.Acad.Sci.USA79, 1588 (1982).

Singer, "Determination of the amount of homology required for recombination in bacteriophage T4." Cell, 31:25-33 (1982).

Smith, et al., Successful Treatment of Experimental *Escherichia coli* Infections in Mice Using Phage: its General Superiority Over Antibiotics, Journal of General Microbiology (Feb. 1982), 128, 307-318.

Smith, et al., "The Control of Experimental *Escherichia coli* Diarrhoea in Calves by Means of Bacteriophages," J. Gen Microbiol (May 1987); 133 (Pt 5):1111-1126.

Smith, "Effectiveness of Phages in Treating Experimental *Escherichia coli* Diarrhoea in Calves, Piglets and Lambs," J. Gen Microbiol (Aug. 1993); 129 (Pt 8):2659-2675.

Smith, "In vitro mutagenesis," Ann. Rev. Genet. 19, 423-462 (1985).

Sonstein et al., "Staphylococcal bacteriophage-associated lysin: a lytic agent active against *Staphylococcus aureus.*" *J Bacteriol*, 107: 499-504. (1971).

Spicer and Konigsberg in Bacteriophage T4 eds. Mathews, Kutter, Mosig and Berget, American Society for Microbiology, Washington, DC, 1983, pp. 299.

Stocker et al, "Immune responses to epitopes inserted in salmonella flagellin," Int. Rev. Immunol. 11, 167 91994).

Stocker, "Aromatic-dependent salmonella as live vaccine presenters of foreign epitopes as inserts in flagellin," Res. Microbiol. 141, 787-796 (1990).

Streisinger et al., "Mutations affecting the lysozyme of phage T4," Cold Spring Harbor Symp. Quant. Biol. 26, 25-30 (1961).

Tourville et al., "Lactic streptococcal phage-associated lysin. I. Lysis of heterologous lactic streptococci by a phage-induced lysin." *J Dairy Sci*, 49: 158-162 91966).

Tsugita et al., "Purification of bacteriophage T4 lysozyme" J. Biol. Chem. 243, 391 (1968).

Vallette et al., "Construction of mutant and chimeric genes using the polymerase chain reaction," Nucleic Acids Res. 17, 723 (1989).

van der Vijver et al., "Induction of mutation in *Staphylococcus aureus* by ethylmethane sulphonate." *J Med Microbiol*, 8: 265-277 (1975).

van Sinderen et al., "Sequence analysis and molecular characterization of the temperate lactococcal bacteriophage r l t." *Mol Microbiol*, 19: 1343-1355 (1996).

Volker et al., Induction of mutations in specific genes of bacteriophage T4 using cloned restriction fragments and marker rescue Mol. Gen. Genet. 177, 447 (1980).

Wang et al., "Holins: The protein clocks of bacteriophage infections," Ann. Rev. Microbiol. 54, 799-825 (2000).

Ward et al., "Sequence analysis of the lysin gene region of the prolate lactococcal bacteriophage c2," *Can J Microbiol*, 39: 767-774 (1993).

Wheeler et al., "Production of group C streptococcus phage-associated lysin and the preparation of *Streptococcus pyogenes* protoplast membranes." *J Gen Microbiol*, 120:27-33 (1980).

Wilson, I. A., et al., "The structure of an antigenic determinant in a protein," Cell 37:767 (1984).

Xu et al. "A signal-arrest-release sequence mediates export and control of the phage PI endolysin", (2004) Proc Natl Acad Sci U S A. 101(17):6415-20.

Yoon et al., "Characterization of a lytic *Lactobacillus plantarum* bacteriophage and molecular cloning of a lysin gene in *Escherichia coli*.," Int J Food Microbiol, 65: 63-74. (2001).

Young, "Bacteriophage lysis: mechanism and regulation." Microbiol Rev, 56:430-481 (1992).

Zhao et al., "Polymerase chain reaction-based point mutagenesis protocol," Methods Enzymol. 217, 218 (1993).

Ziermann et al., "Functions involved in bacteriophage P2-induced host cell lysis and identification of a new tail gene," J. Bacteriol. vol. 176, No. 16, 4974 (1994).

LYSIN-DEFICIENT BACTERIOPHAGES HAVING REDUCED IMMUNOGENICITY

CROSS-REFERENCE TO RELATED APPLICATIONS

This application claims the benefit of prior U.S. Provisional Application Ser. No. 60/325,803, filed Sep. 27, 2001, which application is incorporated herein by reference.

FIELD OF THE INVENTION

The invention relates to bacteriophages, particularly bacteriophages having reduced immunogenicity, and their uses.

BACKGROUND OF THE INVENTION

Bacteriophages are highly specific viruses that infect bacteria. Following infection of a bacterium like E. Coli by a lytic phage, such as T4, a profound rearrangement of all macromolecular syntheses occurs. The RNA Polymerase (RNAP) of the host bacterium binds to the initiation sites of the phage genome known as Immediate-Early (E) genes and transcribes them. Some of the IE gene products degrade the host (bacterial) DNA which lacks the modified base Hydroxy Methyl Cytosine (HMC) while another product ADP-Ribose, binds to the alpha subunits of the bacterial RNAP and renders it incapable of recognizing bacterial cell promoters. This results in the cessation of transcription of host genes. These events occur in the first 3 to 5 minutes after infection.

In the next stage, the modified RNAP recognizes and binds to the so-called Delayed Early (DE) genes, thus eliminating further expression of the IE genes of the phage. The DE gene products are involved in replicating the phage genome using the degraded bacterial DNA bases. One of the products of the DE genes is a novel sigma factor that causes the host RNAP to recognize only the Late (L) genes which are the next to be transcribed. The Late genes are involved in synthesizing new capsid proteins, tails and tail fibers and assembly proteins all of which are needed to assemble progeny phage particles. Finally, the phage lysozyme gene is activated resulting in the lysis of the bacterial host cell and release of the progeny phage.

In view of their highly specific lytic effect, bacteriophages acting on infectious pathogens have been investigated from the time of their discovery to the present day for their therapeutic potential. Soon after their discovery in 1915–17 (d'Herelle. Crit. Rev. Acad. Sci. Paris, 165, 373 (1917)), bacteriophages were used extensively in both the U.S. and Europe for the treatment of bacterial infection. Bacteriophage preparations for treatment of bacterial infections (see, e.g., U.S. Pat. No. 6,121,036) and in inhibition of dental caries (U.S. Pat. No. 4,957,686) have been described. Although highly successful initially, phage therapy are controversial due to lack of quality control, regulatory processes and inadequate understanding of the high specificity of phages for their bacterial hosts. Phage therapy was abandoned in the western world after the advent of antibiotics in the forties. However, in view of the emergence of antibiotic resistance in recent years, there is renewed interest in the development of phage therapy for treating infection (Sulakvelidze et al. Antimicrob Agents Chemotherap, 45, 649, (2001)).

Although the efficacy of phage therapy is widely recognized, there are several problems that need to be addressed before phages can become acceptable therapeutic agents. Many of the problems encountered by the early investigators, such as removal of host bacteria and bacterial debris from therapeutic phage preparations, can be overcome by modern methodologies that have been developed in the past few decades. Basic properties of phages like rapid clearance by the spleen, liver and the reticulo-endothelial system, and the potential for development of antibodies in the human host during treatment, however, require novel solutions if phage therapy is to become generally applicable. One approach for addressing the first problem, namely, rapid clearance, was described by Merrill et al (Proc. Natl. Acad. Sci. USA 93, 3188 (1996) see also U.S. Pat. No. 5,688,501) which involved the selection of long-circulating variants of wild type phages by serial passage in animals.

The generation of neutralizing antibodies after the administration of phages to humans and animals is one of the major concerns that hinders the development of phage therapy, especially for chronic infections. It has been reported that neutralizing antibodies appear a few weeks after the administration of phages to humans or animals (Slopek et al. Arch. Immunol. Ther. Exp., 35, 553 (1987). Administering higher doses of phage has been suggested as a possible solution (Carlton, R. M., Arch. Immunol. Ther. Exp., 47, 267 (1999); however, this is not the most attractive of alternatives. For example, a high-dosing approach requires production of a far greater number of phage for each dose to be administered.

Many studies of potentially therapeutic phages to date have focused on the lytic endpoint that releases progeny phage which can invade other bacterial hosts and destroy them. This amplification provided by the lysis of the bacterial host is an attractive feature of phage therapy, as it facilitates production of more phage and killing of infecting bacteria. However, phage amplification and release through lysis also exposes the subject being treated to a bolus of bacteriophage. This poses the risk that the host will mount an immune response to the phage, which immune response may be undesirable, facilitate clearance of the phage, or both.

During the past decade, the key components essential for host lysis by bacteriophages have been investigated. It is now recognized that two proteins, an endolysin and a holin are needed for host lysis to occur. Endolysins are muralytic enzymes that accumulate in the cytosol and holins are small membrane proteins that regulate access of the endolysins to the cell wall through the cytoplasmic membrane (Wang et al. Ann. Rev. Microbiol. 54, 799–825 (2000)). The lysis gene region of bacteriophage lambda was cloned into a multi-copy plasmid, pBH 20 under the transcriptional control of the lac operator and induction of this "lysis operon" led to lytic behavior parallel to that of bacteriophage infected cells (Garrett, J. et al. Mol. Gen. Genet. 182, 326 (1981). The two lysis genes cph1 and cpl1 of the *Streptococcal pneumoniae* bacteriophage Cp-1, coding for holin and lysin respectively, have been cloned and expressed in *E. coli* (Martin et al. J. Bacteriol. 180, 210 (1998)). Expression of the Cph1 holin resulted in bacterial cell death but not lysis. Concomitant expression of both holin and lysin of phage Cp-1 in *E. coli* resulted in cell lysis. Furthermore, the cph1 gene was able to complement a lambda Sam mutation (carrying an amber mutation in the holin gene) in the nonsuppressing *E. coli* HB101 strain to release phage progeny. Regulated expression of lambda phage lysis genes S and R causes dramatic lysis of both *Vibrio cholerae* and *Salmonella enterica* serovar Typhimurium cells (Jain et al. Infect Immun, 68, 986 (2000).

There is a need in the field for methods and compositions to provide for therapeutic bacteriophage having reduced immunogenicity, and thus reduced clearance, in the host. The present invention addresses this need.

SUMMARY OF THE INVENTION

The present invention features therapeutic bacteriophage deficient in the lysin protein ("Lys minus" phage). Lys minus bacteriophage are incapable of facilitating efficient lysis of the bacterial host since the enzymatic activity of the lysin of the phage is needed for breaking down the peptidoglycan layer of the bacterial cell wall. Lys minus bacteriophage retain activity in invasion of its appropriate bacterial host, destruction of the bacterial genome, and replication, which are sufficient to inhibit bacterial growth and replication. Therefore, the therapeutic Lys minus phage stops the spread of infection by the bacterial pathogen without lysis of the bacterium. This approach is attractive as it also prevents the release of the phage progeny, thus reducing or eliminating the potential for generation of immune responses against the phage. The incapacitated bacterial pathogen is then removed by the normal defense systems such as phagocytes and macrophages.

In one aspect the invention features methods for treating a bacterial infection in an infected subject, the method comprising administering to the subject a Lys minus bacteriophage specific for an infecting bacteria present in the infected subject, where the bacteriophage is administered in an amount effective to inhibit replication of the infecting bacteria and to facilitate a reduction in bacterial load. In specific embodiments, the infecting bacteria are drug resistant bacteria. In other specific embodiments, the bacterial infection is systemic. In further specific embodiments, the infecting bacteria is of a genus selected from the group consisting of *Mycobacteria, Staphylococci, Vibrio, Enterobacter, Enterococcus, Escherichia, Haemophilus, Neisseria, Pseudomonas, Shigella, Serratia, Salmonella, Streptococcus, Klebsiella* and *Yersinia*, and wherein the bacteriophage inhibits growth of the infecting bacteria.

In another aspect the invention features a method for inhibiting growth of bacteria in an infected subject, the method comprising administering to the subject a Lys minus bacteriophage specific for an infecting bacteria present in the infected subject, wherein the bacteriophage is administered in an amount effective to inhibit growth of the infecting bacteria. In specific embodiments, the infecting bacteria are drug resistant bacteria. In other specific embodiments, the bacterial infection is systemic. In further specific embodiments, the infecting bacteria is of a genus selected from the group consisting of *Mycobacteria, Staphylococci, Vibrio, Enterobacter, Enterococcus, Escherichia, Haemophilus, Neisseria, Pseudomonas, Shigella, Serratia, Salmonella, Streptococcus, Klebsiella* and *Yersinia*, and wherein the bacteriophage inhibits growth of the infecting bacteria. In a further related embodiment, the infection involves a mixture of at least two different bacterial hosts and at least two different Lys minus bacteriophage of different host cell specification are administered to treat the mixed infection. The Lys minus bacteriophage, which is defective in lysis of the infecting bacteria, does not cause significant lysis of the infecting bacteria, thereby reducing the number of bacteriophage that are exposed to an immune response by the subject and thus providing for reduced clearance of the bacteriophage relative to that associated with a wild-type bacteriophage.

In another aspect the invention features a pharmaceutical composition comprising an isolated Lys minus bacteriophage and a pharmaceutically acceptable carrier, where upon contacting a bacterial host cell, the Lys minus bacteriophage effects inhibition of growth of the bacterial host cell and is deficient in production of a functional lysin such that the bacteriophage does not effect a substantial level of bacterial host cell lysis. In specific embodiments, the bacteriophage is in lyophilized form. In a related embodiment, the pharmaceutical composition comprises a mixture of defined Lys minus bacteriophage wherein are least two of the phage in the composition have different bacterial host specificity, and which phage mixture is adapted for treating a mixed infection of different bacteria.

In another aspect the invention features a method for treating a bacterial infection in a subject with a therapeutic bacteriophage so as to provide for reduced bacteriophage clearance by the subject's immune system. This is accomplished by administering to a subject having a bacterial infection a Lys minus bacteriophage specific for an infecting bacteria present in the subject, where the bacteriophage is administered in an amount effective to provide for infection of the infecting bacteria by the Lys minus bacteriophage and inhibition of replication of the infecting bacteria. The Lys minus bacteriophage, which is defective in lysis of the infecting bacteria, does not cause significant lysis of the infecting bacteria, thereby reducing the number of bacteriophage that are exposed to an immune response by the subject and thus providing for reduced clearance of the bacteriophage relative to that associated with a wild-type bacteriophage.

In still another aspect, the invention features an isolated Lys minus bacteriophage, which bacteriophage is defective in production of a functional lysin protein. Contacting the bacteriophage with a bacterial host cell for which the bacteriophage is specific results in infection of the bacterial host cell by the Lys minus bacteriophage, replication of the Lys minus bacteriophage, and inhibition of bacterial host cell replication, wherein the Lys minus bacteriophage does not effect lysis of the bacterial host cell by virtue of the action of bacteriophage lysis system.

In another aspect, the invention features a pharmaceutical composition comprising a Lys minus bacteriophage and a pharmaceutically acceptable carrier. Contacting the Lys minus bacteriophage with a bacterial host cell for which the bacteriophage is specific results in inhibition of growth of the bacterial host cell. The bacteriophage may be present in the composition in lyophilized form. In a related embodiment, the pharmaceutical composition comprises a mixture of defined Lys minus bacteriophages, which composition has at least two bacteriophage of different bacterial host specificity, which mixture is particularly suited for treating a mixed infection of different bacteria.

One feature of the invention is that it provides a general procedure to eliminate or minimize the development of an immune response against the phage when it is used for treating bacterial infection.

Another feature of the invention is that it provides methods and compositions to treat bacterial infections, particularly infections by drug-resistant, pathogenic bacteria.

One advantage of the invention is that the use of Lys minus bacteriophages provides for reduced clearance of the bacteriophage to allow for more effective therapy, while at the same time avoiding undesirable immune responses in the subject being treated. Infection of a pathogen with a Lys minus bacteriophage results in the progression of all the events of the phage replication cycle except the last stage, namely, lysis of the bacterial host. The bacterial pathogen infected with a Lys minus phage is incapable of multiplying and spreading the bacterial infection in view of the damage caused by the phage to the bacterial genome. Thus, use of Lys minus bacteriophage results in containing and ultimately eliminating the pathogen with reduced release of phage into the environment or human host during treatment of the infection.

Another advantage of the invention is that the phage-infected bacteria are rendered bacteriostatic in a manner that will not provide for resumption of bacterial replication once therapy is terminated.

Another advantage of the invention is that phage-inactivated bacteria serve as vaccines in situ and an immune response against the incapacitated bacterial pathogen can serve to protect the patient against future infection by the pathogen.

These and other objects, advantages, and features of the invention will become apparent to those persons skilled in the art upon reading the details of the compositions and methods of their use as more fully described below.

Figure 1:
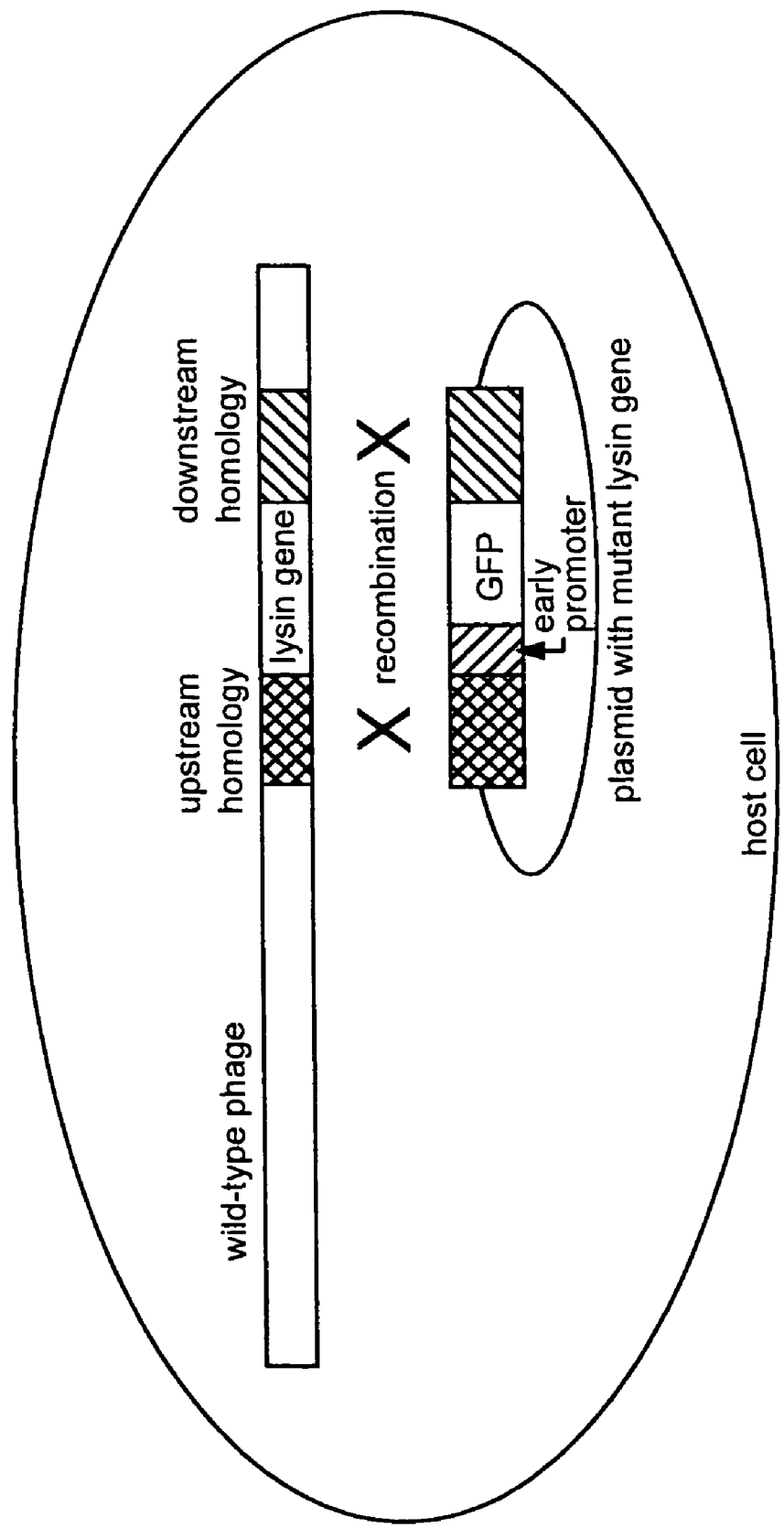
FIG. 1 is a schematic showing the use of a bacterial host having a plasmid with a mutant lysin gene for use in production of therapeutic phage of the invention.

Before the present invention is described, it is to be understood that this invention is not limited to particular methodology, protocols, bacteriophage, bacterial pathogens, animal species or genera, constructs, and reagents described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a bacteriophage" includes a plurality of such bacteriophage and reference to "the host cell" includes reference to one or more host cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

Although the potential of phage therapy for treating antibiotic resistance is generally acknowledged, the development of phage therapy has lagged due to the controversy surrounding the use of phages in the 1920s and 1930s, as well as concerns about the potential for immune responses against therapeutic phage. The production of well-defined and well-characterized phage using modern technologies and current standards of quality control have addressed the issues that led to controversies about phage therapy in the past. However, the potential for generating immune responses is a fundamental property of bacteriophages and prevention of the immune response or reduction of this potential is important for effective application of phage therapy. The use of therapeutic bacteriophages in the treatment of bacterial infection is, in some regards, a race between the bacteriophage as it infects the bacteria of the subject's infection and the immune response as it recognizes the bacteriophage as foreign and attempts to clear the bacteriophage from the body. The object of this invention is to provide a procedure to delay, minimize, or eliminate (avoid) the development of an immune response against the phage when it is used for treating bacterial infection.

The present invention accomplishes this objective by providing Lys minus (Lys⁻) phages which can infect bacteria and inhibit bacterial growth, but which phage can not effect lysis of the infected bacterium. The bacteriophages of the invention in essence act as antimicrobial agents that inhibit bacterial replication, without effecting lysis of the bacterial host. By reducing the number of bacteriophage to which the subject undergoing therapy is exposed, the host immune response against the therapeutic bacteriophage will be less robust, thus reducing the clearance rate of the therapeutic phage.

Antibiotics exert their action either by killing the bacteria (bactericidal) or by inhibiting the growth of the bacteria (bacteriostatic). Although bactericidal agents are preferred, bacteriostatic agents have also been beneficial, since the normal defenses of the host can then destroy the weakened bacteria. Specific invasion of a bacterial pathogen by genetically modified bacteriophage proposed in this invention incapacitate the pathogen, which pathogen would then be eliminated by the normal defense mechanisms of the host. In contrast to bacteriostatic antimicrobial agents in which withdrawal of therapy can lead to the resumption of the infection, phage-inactivated bacteria remain non-viable and cannot resume infection.

The Lys minus phage of the invention can be used to inactivate any specific bacterial host and, therefore, can be developed as a therapeutic agent for the treatment of any bacterial infection. The present invention is thus applicable to all bacteriophages.

Specific aspects of the invention will now be described in more detail.

Definitions

By "bacteriophage" and "phage", which terms are used interchangeably herein, is meant any of a variety of viruses that have a specific affinity for and infect bacteria. These thus include, coliphages, which infect *Escherichia coli* (e.g., lambda phage and the T even phages, T2, T4 and T6). Phages generally are composed of a protein coat or capsid enclosing the genetic material, DNA or RNA, that is injected into the bacterium upon infection. In the case of virulent phages all synthesis of host DNA, RNA and proteins ceases and the phage genome is used to direct the synthesis of phage nucleic acids and proteins using the host's transcriptional and translational apparatus. These phage components then self assemble to form new phage particles. The synthesis of a phage lysozyme leads to rupture of the bacterial cell wall releasing, typically 100–200 phage progeny. The temperate phages, such as lambda, may also show this lytic cycle when they infect a cell, but more frequently they induce lysogeny, in which the phage integrates into the bacterial host DNA to persist as a prophage. In general, the bacteriophage of interest in the invention are lytic phages rather than temperate phages.

By "Lys minus phage" or "Lys minus bacteriophage", which terms are used interchangeably herein, is meant a phage deficient in lysin protein. Lys minus bacteriophage are incapable of facilitating efficient lysis of the bacterial host since the enzymatic activity of the lysin of the phage is needed for enzymatic degradation of the peptidoglycan layer of the bacterial cell wall. Lys minus bacteriophage retain activity in infection of its appropriate bacterial host, destruction of the bacterial genome, and replication, which are sufficient to inhibit bacterial growth and replication. Lys minus phage include those generated by mutating or deleting the gene encoding the lysin of the phage lysis system. Lys minus phage encompasses phage defective in lysin due to deletion of all or a portion of the lysin-encoding nucleic acid so that no detectable lysin is produced, or a truncated form of lysin is produced which has decreased activity in facilitating lysis (e.g., the truncated lysin is ineffective in promoting efficient lysis of the bacterial host, or does not facilitate any detectable wild-type lysin-mediated lysis activity). Lys minus phage also include those in which a lysin-encoding nucleic acid is operably linked to an inducible promoter such that lysin production occurs at a level effective to induce lysis only when in the presence of an agent which activates the inducible promoter. Preferably, the inducer agent is one that is not normally found in a host to be treated using the phage, e.g., the inducer is not an agent that is endogenous to a host to be treated.

Lys minus phage also include phage that produce modified lysin protein, which lysin is defective in promoting bacterial lysis due to the presence of one or more mutations. Such mutations include at least one, or any combination of one or more, nucleic acid deletions, substitutions, additions, or insertions which result in an alteration in the corresponding amino acid sequence of the encoded lysin protein.

By "isolated" is meant that the material is at least 60%, by weight, free from the proteins and naturally-occurring organic molecules with which it is naturally associated. Preferably, the material is at least 75%, more preferably at least 90%, and most preferably at least 99%, by weight, the material of interest. "Isolated" thus encompasses preparations that are enriched for the desired material.

The terms "polynucleotide" and "nucleic acid", used interchangeably herein, refer to a polymeric forms of nucleotides of any length, either ribonucleotides or deoxynucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "polypeptide" and "protein", used interchangeably herein, refer to a polymeric form of amino acids of any length, which can include coded and non-coded amino acids, chemically or biochemically modified (e.g., post-translational modification such as glycosylation) or derivatized amino acids, polymeric polypeptides, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "recombinant polynucleotide" as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

"Recombinant host cells", "host cells", "cells", "cell lines", "cell cultures", and other such terms denoting microorganisms or higher eukaryotic cells cultured as unicellular entities refer to cells which can be, or have been, used as recipients for recombinant vector or other transfer DNA, and include the progeny of the original cell which has been transfected. It is understood that the progeny of a single parental cell may not necessarily be completely identical in morphology or in genomic or total DNA complement as the original parent, due to natural, accidental, or deliberate mutation.

"Operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences.

An "open reading frame" (ORF) is a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to mRNA, cDNA, and recombinant polynucleotide sequences.

"Heterologous" means that the materials are derived from different sources (e.g., from different genes, different species, etc.).

"Transformation", as used herein, refers to the insertion of an exogenous polynucleotide into a host cell, irrespective of the method used for the insertion, for example, direct uptake, transduction, f-mating or electroporation. The exogenous polynucleotide may be maintained as a non-integrated vector, for example, a plasmid, or alternatively, may be integrated into the host genome.

The terms "individual," "subject," "host," and "patient," are used interchangeably herein and refer to any subject having a bacterial infection amenable to treatment using the therapeutic bacteriophage of the invention, and for whom treatment or therapy is desired. Mammalian subjects and patients, particularly human subjects or patients are of particular interest. Other subjects may include cattle, dogs, cats, guinea pigs, rabbits, rats, mice, horses, and so on.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease (e.g., eliminating an infection, reducing the severity of an infection, reducing bacterial load, inhibiting growth of bacteria, etc.). "Treatment" as used herein covers any treatment of a disease in a subject, particularly a mammalian subject, more particularly a human, and includes: (a) preventing the disease or symptom from occurring in a subject which may be predisposed to the disease or symptom but has not yet been diagnosed as having it; (b) inhibiting the disease symptom, i.e., arresting its development; or relieving the disease symptom, i.e., causing regression of the disease or symptom.

By "infecting bacterium" is meant a bacterium that has established infection in the host, and which may be associated with a disease or undesirable symptom as a result. Generally, infecting bacteria are pathogenic bacteria.

By "drug-resistant bacteria" or "antibiotic-resistant bacteria" is meant a bacterial strain that is resistant to growth inhibition or killing by an antibiotic. Multi-drug resistant bacteria are resistant to two or more antibiotics. Drug resistance can encompass, for example, ineffective killing of the infecting bacteria such that at least an infectious dose remains in the subject and the infection continues, resulting in continued symptoms of the associated infectious disease or later evidence of such symptoms. Drug resistance can also encompass inhibiting growth of the drug-resistant bacteria until such time therapy is discontinued, after which the bacteria begin to replicate and further the infectious disease.

By "inhibition of bacterial growth" in the context of infection of a bacterial cell with a Lys minus bacteriophage is meant that, following infection of the bacteria, the bacteriophage inhibits or interferes with the bacterial host cell's normal transcriptional and/or translational mechanisms such that the infected bacteria does not undergo substantial cell division (replication) and is caused to enter a state of bacteriostasis.

Bacteriophage for Production of Lys Minus Bacteriophage

A Lys minus phage of the invention can be generated from any wild-type bacteriophage, preferably from a lytic phage. Thus, the methods and compositions of the invention can be applied to the development of any of a variety of Lys minus bacteriophages which are specific for any of a variety of bacteria, and thus useful in the treatment of a wide variety of bacterial infection. While it is contemplated that the present invention can be used to treat any bacterial infection in an animal, the invention finds particular use in therapy (adjunctive or stand-alone) for infections caused by drug-resistant bacteria. Exemplary drug-resistant, clinically-important bacterial species and strains are listed below. The American Type Culture Collection (ATCC, Manassas, Md.) accession number for an exemplary wild-type bacteriophage infecting the corresponding clinically-relevant strains are provided following the strain it infects. Such phage are exemplary of those that can be modified to be Lys minus to provide the therapeutic bacteriophage according to the invention. The list is as follows:

1. All clinically important members of the family Enterobacteriaceae, including, but not limited to:
   a. All clinically important strains of *Escherichia*, with *E. coli* being of particular interest (ATCC phage #23723-B2);
   b. All clinically important strains of *Klebsiella*, with *K. pneumoniae* (ATCC phage #23356-B1) being of particular interest;
   c. All clinically important strains of *Shigella*, with *S. dysenteriae* being of particular interest (ATCC phage #11456a-B1);
   d. All clinically important strains of *Salmonella*, including *S. abortus-equi* (ATCC phage #9842-B1), *S. typhi* (ATCC phage #19937-B1), *S. typhimurium* (ATCC phage #19585-B1), *S. newport* (ATCC phage #27869-B1), *S. paratyphi-A* (ATCC phage #12176-B1), *S. paratyphi*-B (ATCC phage #19940-B1), *S. potsdam* (ATCC phage #25957-B2), and *S. pollurum* (ATCC phage #19945-B1);
   e. All clinically important strains of *Serratia*, most notably *S. marcescens* (ATCC phage #14764-B1)
   f. All clinically important strains of *Yersinia*, most notably *Y. pestis* (ATCC phage #11953-B1)
   g. All clinically important strains of *Enterobacter*, most notably *E. cloacae* (ATCC phage #23355-B1);
2. All clinically important *Enterococci*, most notably *E. faecalis* (ATCC phage #19948-B1) and *E. faecium* (ATCC phage #19953-B1)
3. All clinically important *Haemophilus* strains, most notably *H. influenzae* (exemplary phage can be obtained from the World Health Organization (WHO) or other labs that make them available publicly);
4. All clinically important *Mycobacteria*, most notably *M. tuberculosis* (ATCC phage #25618-B1), *M. avium-intracellulare*, *M. bovis*, and *M. leprae*. (exemplary phage available commercially from WHO, via The National Institute of Public Healthy & Environmental Protection, Bilthoven, The Netherlands);
5. *Neisseria gonorrhoeae* and *N. meningitidis* (exemplary phage can be obtained publicly from WHO or other sources);
6. All clinically important *Pseudomonads*, with *P. aeuruginosa* being of particular interest (ATCC phage #14203-B1);
7. All clinically important *Staphylococci*, with *S. aureus* (ATCC phage #27690-B1) and *S. epidermidis* (exemplary phage available publicly through the WHO, via the Colindale Institute in London) being of particular interest;
8. All clinically important *Streptococci*, wit *S. pneumoniae* being of particular interest (exemplary phage can be obtained publicly from WHO or other sources); and
9. *Vibrio cholera* (Phage #14100-B1)

Additional bacterial pathogens, far too numerous to mention here, particularly those in which drug-resistance has developed, can also be susceptible to therapy according to the present invention. In short, all bacterial infections caused by bacteria for which there is a corresponding phage either currently available or for which phage can be identified, can be treated using the present invention by rendering the corresponding phage Lys minus, and contacting the bacteria with the Lys minus phage.

Novel phage can also be used in the present invention. Such novel phages are continuously isolated from hospital sewage and other sources by standard procedures. Typically, 9 ml of the sewage sample is mixed with 1 ml of 10×LB broth, 0.1 ml of overnight LB broth shake culture growth of target bacterial strain is added and incubated overnight at 37° C. Chloroform (0.1 ml) is added and incubated at 37° C. for 15 minutes with shaking at 300 rpm. This is then centrifuged at 14,000 rpm for 20 minutes at 4 C and the supernatant is stored in sterile Eppendorf tubes. These crude phage preparations are further purified and characterized as needed.

Phage Lysins

Lysis of the host bacterial cell by many types of bacteriophages depends on at least two different sets of proteins (Young et al. Microbiol. Rev. 56, 430 (1992)). Degradation of the bacterial cell wall is accomplished by the lysins. The best studied examples are the T4 e gene product, a lysozyme (Tsugita et al. J. Biol. Chem. 243, 391 (1968)) and the lambda R protein, a transglycosylase (Garrett et al. Mol. Gen. Genet. 182, 326 (1981)). The lysin genes of a large number of bacteriophages have been identified and characterized in the past decade. These include the lysins of bacteriophage T7 (Inouye et al. Biol. Chem. 248, 7247 (1973), gp 19 from *Salmonella typhimurium* phage P22 (Rennell et al. Virol. 143, 280 (1985), phi 29 gp 15 from two phages of the gram-positive bacteria *Lactococcus lactis* and *Bacillus subtilis* (Garvey et al. Nucleic Acids Res. 14, 10001 (1986)), the Pneumococcal bacteriophage Cp-1 (Garcia et al. J. Virol. 61, 2573 (1987)), the *Pseudomonas* phage f6 (Caldentey et al. Biochim. Biophys. Acta 1159, 44 (1992)), the K gene of bacteriophage P2 (Ziermann et al. J. Bacteriol. 176, 4974 (1994)), gene 17 of bacteriophage P1 (Schmidt et al. Bacteriol. 178, 1099 (1996)), the *Listeria monocytogenes* bacteriophage lysins Ply 511 and Ply 518 (Gaeng et al. Appl. Environ. Microbiol. 66, 2951 (2000)) as well as numerous phages infecting *Lactobacilli* (Shearman et al. Appl. Environ. Microbiol. 60, 3063 (1994)); Henrich et al. J. Bacteriol. 177, 723 (1995)).

Additional phage lysins reported in the literature are given below.

Ackermann (1998) Tailed bacteriophages: the order caudovirales. *Adv Virus Res*, 51:135–201.

Arendt et al. (1994) Molecular characterization of lactococcal bacteriophage Tuc2009 and identification and analysis of genes encoding lysin, a putative holin, and two structural proteins. *Appl Environ Microbiol*, 60: 1875–1883.

Auad et al. (1999) Physical mapping and partial genetic characterization of the *Lactobacillus delbrueckii* subsp. *bulgaricus* bacteriophage 1b539. *Arch Virol*, 144: 1503–1512.

Boizet et al. (1990) Cloning, expression and sequence analysis of an endolysin-encoding gene of *Lactobacillus bulgaricus* bacteriophage mv1. *Gene*, 94: 61–67.

Calandra et al. (1980) Lysis and protoplast formation of group B streptococci by mutanolysin. *Infect Immun*, 28: 1033–1037.

Calandra et al. (1975) Cellular streptolysin S-related hemolysins of group A *Streptococcus* C203S. *Infect Immun*, 12: 13–28.

Chandry et al. (1997) Analysis of the DNA sequence, gene expression, origin of replication and modular structure of the *Lactococcus lactis* lytic bacteriophage skl. *Mol Microbiol*, 26: 49–64.

Cohen et al. (1975) Simple procedure for production by group C streptococci of phage-associated lysin active against group A streptococci. *Appl Microbiol*, 29: 175–178.

Coleman et al. (1986) Cloning and expression in *Escherichia coli* and *Staphylococcus aureus* of the beta-lysin determinant from *Staphylococcus aureus*: evidence that bacteriophage conversion of beta-lysin activity is caused by insertional inactivation of the beta-lysin determinant. *Microb Pathog*, 1: 549–564.

Coleman et al. (1989) *Staphylococcus aureus* bacteriophages mediating the simultaneous lysogenic conversion of beta-lysin, staphylokinase and enterotoxin A: molecular mechanism of triple conversion. *J Gen Microbiol*, 135: 1679–1697.

Cooney et al. (1988) Molecular cloning and genetic analysis of the determinant for gamma-lysin, a two-component toxin of *Staphylococcus aureus*. *J Gen Microbiol*, 134:2179–2188.

de Ruyter et al. (1997) Food-grade controlled lysis of *Lactococcus lactis* for accelerated cheese ripening. *Nat Biotechnol*, 15: 976–979.

Diaz et al. (1996) The two-step lysis system of pneumococcal bacteriophage EJ-1 is functional in gram-negative bacteria: triggering of the major pneumococcal autolysin in *Escherichia coli*. *Mol Microbiol*, 19: 667–681.

Dietrich et al. (1998) Delivery of antigen-encoding plasmid DNA into the cytosol of macrophages by attenuated suicide *Listeria monocytogenes*. *Nat Biotechnol*, 16: 181–185.

Elias et al. (1980) *Staphylococcus aureus* haemolysins: their use in strain typing. *Acta Microbiol Acad Sci Hung*, 27: 183–190.

Fischetti et al. (1971) Purification and physical properties of group C streptococcal phage-associated lysin. *J Exp Med*, 133: 1105–1117.

Garcia et al. (1987) Cloning, purification, and biochemical characterization of the pneumococcal bacteriophage Cp-1 lysin. *J Virol*, 61: 2573–2580.

Garcia et al. (1983) Mechanism of phage-induced lysis in pneumococci. *J Gen Microbiol*, 129: 479–487.

Garcia et al. (1984) Biochemical characterization of a murein hydrolase induced by bacteriophage Dp-1 in *Streptococcus pneumoniae*: comparative study between bacteriophage-associated lysin and the host amidase. *J Bacteriol*, 159: 793–796.

Gindreau et al. (1999) Molecular analysis of the region encoding the lytic system from *Oenococcus oeni* temperate bacteriophage phi 10MC. *FEMS Microbiol Lett*, 171: 231–238.

Henrich et al. (1995) Primary structure and functional analysis of the lysis genes of *Lactobacillus gasseri* bacteriophage phi adh. *J Bacteriol*, 177: 723–732.

Hill et al. (1981) Identification of a lysin associated with a bacteriophage (A25) virulent for group A streptococci. *J Bacteriol*, 145: 696–703.

Kaneko et al. (1998) Complete nucleotide sequence and molecular characterization of the temperate staphylococcal bacteriophage phiPVL carrying Panton-Valentine leukocidin genes. *Gene*, 215:57–67.

Kuhnemund (1972) Studies on the lysis of *streptococcus pyogenes* (group A, type 1) by phage-associated lysin (author's transl). *Z Immunitatsforsch Exp Klin Immunol*, 143: 184–191.

Loessner et al. (1996) Modified *Listeria* bacteriophage lysin genes (ply) allow efficient overexpression and one-step purification of biochemically active fusion proteins. *Appl Environ Microbiol*, 62: 3057–3060.

Loessner et al. (1995) Heterogeneous endolysins in *Listeria monocytogenes* bacteriophages: a new class of enzymes and evidence for conserved holin genes within the siphoviral lysis cassettes. *Mol Microbiol*, 16: 1231–1241.

Martin et al. (1998) Functional analysis of the two-gene lysis system of the pneumococcal phage Cp-1 in homologous and heterologous host cells. *J Bacteriol*, 180:210–217.

Mindich et al. (1979) Cell wall lysin as a component of the bacteriophage phi 6 virion. *J Virol*, 30: 489–496.

Mullan et al. (1985) Lysin production by phi C2(W), a prolate phage for *Streptococcus lactis* C2. *J Dairy Res*, 52: 113–121.

Mullan et al. (1985) Partial purification and some properties of phi C2(W) lysin, a lytic enzyme produced by phage-infected cells of *Streptococcus lactis* C2. *J Dairy Res*, 52:123–138.

Nelson et al. (2001) Prevention and elimination of upper respiratory colonization of mice by group A streptococci by using a bacteriophage lytic enzyme. *Proc Natl Acad Sci USA*, 98: 4107–4112.

Oki et al. (1996) Cloning, sequence analysis, and expression of the genes encoding lytic functions of Bacteriophage phi gle. *Gene*, 176: 215–223.

Payne et al. (1996) Exploitation of a chromosomally integrated lactose operon for controlled gene expression in *Lactococcus lactis*. *FEMS Microbiol Lett*, 136: 19–24.

Raina (1981) Purification of *Streptococcus* group C bacteriophage lysin. *J Bacteriol*, 145: 661–663.

Sable et al. (1995) The lysins of bacteriophages infecting lactic acid bacteria. *Appl Microbiol Biotechnol*, 43: 1–6.

Sanders et al. (1997) A chloride-inducible gene expression cassette and its use in induced lysis of *Lactococcus lactis*. *Appl Environ Microbiol*, 63: 4877–4882.

Shearman et al. (1989) Cloning and DNA sequence analysis of a *Lactococcus* bacteriophage lysin gene. *Mol Gen Genet*, 218: 214–221.

Shearman et al. (1994) Controlled expression and structural organization of a *Lactococcus lactis* bacteriophage lysin encoded by two overlapping genes. *Appl Environ Microbiol*, 60: 3063–3073.

Sheehan et al. (1996) Analysis of the catalytic domain of the lysin of the lactococcal bacteriophage Tuc2009 by chimeric gene assembling. *FEMS Microbiol Lett*, 140: 23–28.

Sheehan et al. (1997) The lytic enzyme of the pneumococcal phage Dp-1: a chimeric lysin of intergeneric origin. *Mol Microbiol*, 25: 717–725.

Sheehan et al. (1999) Identification and characterization of a lysis module present in a large proportion of bacteriophages infecting *Streptococcus thermophilus*. *Appl Environ Microbiol*, 65: 569–577.

Sonstein et al. (1971) Staphylococcal bacteriophage-associated lysin: a lytic agent active against *Staphylococcus aureus*. *J Bacteriol*, 107: 499–504.

Tourville et al. (1966) Lactic *streptococcal* phage-associated lysin. I. Lysis of heterologous lactic streptococci by a phage-induced lysin. *J Dairy Sci*, 49: 158–162.

van der Vijver et al. (1975) Induction of mutation in *Staphylococcus aureus* by ethylmethane sulphonate. *J Med Microbiol*, 8: 265–277.

van Sinderen et al. (1996) Sequence analysis and molecular characterization of the temperate lactococcal bacteriophage rlt. *Mol Microbiol*, 19: 1343–1355.

Ward et al. (1993) Sequence analysis of the lysin gene region of the prolate lactococcal bacteriophage c2. *Can J Microbiol*, 39: 767–774.

Wheeler et al. (1980) Production of group C *streptococcus* phage-associated lysin and the preparation of *Streptococcus pyogenes* protoplast membranes. *J Gen Microbiol*, 120:27–33.

Yoon et al. (2001) Characterization of a lytic *Lactobacillus plantarum* bacteriophage and molecular cloning of a lysin gene in *Escherichia coli*. *Int J Food Microbiol*, 65: 63–74.

Young (1992) Bacteriophage lysis: mechanism and regulation. *Microbiol Rev*, 56:430–481.

Where the lysin gene of a bacteriophage of interest has not yet been identified, such identification can be accomplished using methods routine in the art. Bacteriophage lysin genes can be identified by, for example, methods based upon sequencing of the bacteriophage genome, and comparison of the sequence to those of bacteriophage in which the lysin gene has been described. Comparison of the amino acid sequences of the lysins described to date reveals three conserved regions (Schmidt et al. J. Bacteriol. 178, 1099 (1996). The first conserved region contains the catalytic site with the EG sequence and the active-site cleft. The lysin genes of newly isolated bacteriophages, or bacteriophages in which the lysin gene has not yet been described, can be identified and isolated by nucleic acid amplification techniques (e.g., PCR) using primers corresponding to the nucleotide sequences from the conserved regions of known lysin genes. Using conserved parts of the lysin gene, the lysin genes from any phage can be isolated, using degenerate oligos homologous to any two of the three conserved regions. Once this PCR product is sequenced, new primers can be designed to sequence the regions upstream and downstream of the lysin genes, using phage DNA as template for sequencing.

Generation Of Mutant Lys Minus Phases

Lys minus phage can be generated in any of a variety of ways consistent with providing a lysis-defective phage according to the invention. Preferably Lys minus phage are generated by modifying the bacteriophage genome so that the bacteriophage is deficient in wild-type lysin (Lys) protein or so that the bacteriophage contains a functional lysin gene operably linked to an inducible promoter. Alternatively, bacteriophage have reduced levels of lysin, and thus reduced lysis rates, can be selected by screening for phage that infect bacteria and inhibit replication of the bacterial host, but which have reduced rates of lysis, e.g., the bacteriophage act as bacteriostatic agents of the bacterial host, but do not lyse the bacterial host cell at a rate or level associated with a wild-type phage that is not deficient in the phage lysis system.

Bacteriophage deficient in the lysin protein ("Lys minus" phage), include those generated by mutating or deleting the gene encoding the lysin of the phage lysis system. "Lys minus" phage encompasses phage defective in lysin due to deletion of all or a portion of the lysin-encoding nucleic acid so that no detectable lysin is produced, or a truncated form of lysin is produced which has decreased activity in facilitating lysis (e.g., the truncated lysin is ineffective in promoting efficient lysis of the bacterial host, or does not facilitate any detectable wild-type lysin-mediated lysis activity). "Lys minus" phage also include phage that produce modified lysin protein, which lysin is defective in promoting bacterial lysis due to the presence of one or more mutations. Such mutations include at least one, or any combination of one or more, nucleic acid deletions, substitutions, additions, or insertions which result in an alteration in the corresponding amino acid sequence of the encoded lysin protein.

Lys minus phage also include those in which the gene encoding lysin has been modified such that the gene is operably linked to an inducible promoter so that lysin is only produced when the phage is contacted with an agent that activates the inducible promoter. Such Lys minus phage can be produced by modifying the wild-type lysin gene to include an inducible promoter, by replacing the lysin gene with a lysin-encoding nucleic acid operably linked to an inducible promoter; or by mutating or deleting the gene encoding lysin and inserting into the phage a lysin-encoding nucleic acid operably linked to an inducible promoter.

Bacteriophage having defective lysin can be generated using classical microbiological methods, such as plaque morphology assays (see, e.g., Streisinger et al. Cold Spring Harbor Symp. Quant. Biol. 26, 25 (1961)).

Lys minus phage can also be generated using recombinant techniques, such as site-directed mutagenesis (Smith Ann. Rev. Genet. 19, 423 (1985)), e.g., using nucleic acid amplification techniques such as PCR (Zhao et al. Methods Enzymol. 217, 218 (1993)) to introduce facile deletions, insertions and point mutations. Other methods for deletion mutagenesis involve, for example, the use of either BAL 31 nuclease, which progressively shortens a double-stranded DNA fragment from both the 5' and 3' ends, or exonuclease III, which digests the target DNA from the 3' end (see, e.g., Henikoff Gene 28, 351 (1984)). The extent of digestion in both cases is controlled by incubation time or the temperature of the reaction or both. Point mutations can be introduced by treatment with mutagens, such as sodium bisulfite, which deaminates deoxycytidine to deoxyuridine resulting in the substitution of an A:T base pair for a G:C base pair in approximately 50% of the template molecules after one round of replication (Botstein et al. Science 229, 1193 (1985)).

Other exemplary methods for introducing point mutations involve enzymatic incorporation of nucleotide analogs or misincorporation of normal nucleotides or alpha-thionucleotide by DNA polymerases (Shortle et al. Proc. Natl. Acad. Sci. USA79, 1588 (1982)). In oligonucleotide-directed mutagenesis, the target DNA is cloned into an M13 vector to produce single-stranded wild-type DNA template to which the oligo mutagen is annealed. This produces a noncomplementary (looped out) region on the oligo primer or on the template, resulting in an insertion or a deletion, respectively. Base pair mismatch between the template and the primer results in point mutagenesis. PCR-based mutagenesis methods (or other mutagenesis methods based on nucleic acid amplification techniques), are generally preferred as they are simple and more rapid than classical techniques described above (Higuchi et al. Nucleic Acids Res. 16, 7351 (1988); Vallette et al. Nucleic Acids Res. 17, 723 (1989)).

Bacteriophage defective in lysin can be identified by screening candidate phage by, for example, comparing the ability of the candidate phage to lyse a wild-type bacterial host to the ability of the candidate phage to lyse a recombinant bacterial host modified to express the lysin protein (e.g., by a helper phage, from an introduced helper plasmid encoding the phage's lysin, or from a recombinant phage lysin-encoding sequence integrated in the bacterial host's genome). Candidate phage that lyse the lysin-expressing bacterial host, but that fail to effect, or do not efficiently effect, lysis of the wild-type bacterial host represent exemplary Lys minus phage suitable for use in the invention.

One approach of particular interest for generating Lys minus phages totally lacking the lysozyme activity of the lysin gene is to delete the first conserved region which contains the catalytic site and the active site cleft. Based on the nucleotide sequence of the lysin, PCR product(s) lacking the conserved region I are generated and transformed into the appropriate bacterial host together with the wild-type phage. A selectable marker, such as the jellyfish green fluorescent protein (GFP, Chalfie, M. et al, Science 263, 802, 1994), can be used instead of an antibiotic resistance marker. Antibiotic resistance markers may prove undesirable where the phage is to be used in therapy, particularly where the phage therapy is to be provided in combination with antibiotics. Replicas of the resistance bacteria (to avoid UV mutagenesis) are then screened under UV light for those expressing GFP.

Production Of Lys Minus Phases Using Marker Rescue Techniques

In another embodiment, Lys minus phage having a desired defect in the lysin gene are generated using marker rescue techniques. The technique of marker rescue has been used extensively to map mutations in phage, and to transfer artificially-generated mutations from phage genes cloned in a plasmid to the phage genome (Volker et al. Mol. Gen. Genet. 177, 447 (1980)). Exemplary of the use of this technique is the application to identify genes involved in T4 phage assembly and maturation. Specifically, restriction fragments containing the T4 phage assembly and maturation genes 20 to 22 were cloned in plasmids, mutagenized, and the mutations were then recombined back into the phage genome by infection of *E. coli* carrying the plasmid with a T4 20/21 am (amber) double mutant (Volker, supra, 1980). The phage progeny that had undergone recombination with the plasmid were selected by plating on a su⁻ host (lacking an amber suppressor) allowing the selection of recombinant phage. These am⁺ phages, were then screened non-selectively for the desired temperature-sensitive mutations in genes 20 and 21.

A similar strategy can be employed for the lysin gene. The mutant lysin gene (either a non-functional lysin gene or a functional lysin gene operably linked to an inducible promoter), which can be generated using recombinant techniques described above, is cloned into a plasmid having a selectable marker, e.g., ampicillin-resistance. Two types of bacterial hosts containing plasmids with either wild-type (WT lysin host) or mutant lysin genes (mutant lysin host) are used. The former strain containing the wild type lysin gene is used as the helper strain for large scale production of mutant Lys minus phage, where the Lys-minus phage is one lacking an inducible lysin gene. The latter strain containing the mutant lysin gene is used to introduce Lys-mutations in wild-type phage. FIG. 1 provides a schematic of a bacterial host cell having a mutant lysin gene useful in generating Lys minus phage of the invention.

Recombinant, mutant lysin-expressing bacterial hosts for production of Lys minus phages (as illustrated in FIG. 1) can be generated by using methods well known in the art. For example, the sequences of the regions flanking the lysin gene (about 100 bp on each side) in each of the phages to be mutated are isolated. Generally, at least about 50 bp homology is provided on each side, flanking the region of interest encoding the phage lysin gene (Singer (1982) Cell, 31: 25–33). The DNAs corresponding to the upstream and downstream regions of each phage lysin gene is isolated by nucleic acid amplification (e.g., PCR) and cloned into a plasmid having a first selectable marker (e.g., ampicillin resistance) with a suitable restriction site between two regions for insertion of a DNA cassette in which a second selectable marker (e.g., GFP) is expressed from an early promoter of the same phage. This plasmid is introduced into appropriate bacterial host cells by transformation and selection for the first selectable marker (exemplified here by ampicillin resistance). An exemplary plasmid with a mutant lysin gene useful in this technique is shown in FIG. 1. Alternatively, the construct of the plasmid may be genomically integrated in the bacterial host genomic DNA.

The bacterial host harboring the mutant lysin gene is infected with wild-type phage at a low multiplicity of infection. As the phage replicates, some of the phage recombine by a double crossover event with the mutant lysin gene in the bacterial host to yield Lys minus phage. Since it is likely that recombination in any cell will not be 100% efficient, there may be wild-type phage in the same cells as the Lys minus phage. The wild-type virus will act as helper virus to cause lysis of infected cells whether or not recombination occurs.

The two types of viruses are collected by lysing the bacterial cells with chloroform, and the Lys minus phage purified away from the wild-type virus by plaque purification. The virus from each plaque is then tested to see if it is wild-type or Lys minus. Testing to identify Lys minus phage can be accomplished by, for example, examining the ability of the phage from each plaque to infect and kill two types of host cells as detected by plaque formation. One type of host cell is the normal (wild-type) host bacterium, the other is the wild-type lysin host bacterium described above. Wild-type phage will effectively lyse and kill both types of hosts, while Lys minus phage kills only the host cells expressing lysin.

Where the Lys minus phage expresses a detectable marker (e.g., GFP), and particularly where the selectable marker is expressed from a viral early promoter, fluorescent plaques representing Lys minus phage can be visualized directly during plaque purification. The Lys minus phenotype of these phage can then be confirmed by screening as described above.

Generation Of Wild-Type Lysin Host for Scale-Up Production of Lys Minus Phage

Lys minus phages can replicate and assemble in their host bacteria but, by definition, will not be able to lyse the host and release the progeny phages efficient. For the production of therapeutic Lys minus phages, release of the modified phages from the bacterial host is essential. Where the Lys minus phage is one in which a lysin gene is under control of an inducible promoter, lysis of the bacterial host can be accomplished by contacting the phage with an agent or environmental condition that activates the inducible promoter, thereby inducing lysin production and consequent lysis of the host bacteria cells.

Lysis of the host bacteria and release of the Lys minus phage can also be accomplished by introducing a helper plasmid carrying a lysin gene under an inducible promoter into the bacterial host. Previous studies have shown that expression of phage lambda lysis genes in E. coli results in a sharply defined lysis (Garrett et al. Mol. Gen. Genet. 182, 326, 1981). Recently, lambda phage S and R gene products (holin and lysin respectively) have been used in an inducible lysis system (Jain et al. Infection & Immunity 68, 986, 2000). Thus, large quantities of Lys minus phages can be produced in appropriate hosts containing a helper plasmid carrying a lysin gene coding for a highly potent lysozyme (e.g. T4 lysozyme) under an inducible promoter.

Lysin genes from any of the sequenced phages can be isolated by nucleic acid amplification techniques (e.g., PCR) and cloned in plasmid having a selectable marker (e.g., antibiotic resistance such as ampicillin resistance) so that they are expressed from an inducible promoter using standard recombinant DNA procedures. The lysin gene chosen will be one with the least amount of homology to the phage lysin gene to avoid recombination between the Lys minus phage and the lysin gene in the host strain to produce wild-type recombinants. The efficacy of production of only Lys minus phages is tested by confirming that the Lys minus phage stock does not produce plaques on a host strain lacking the lysin gene. If necessary, a variety of helper host strains expressing lysin from different sources and inducible promoters can be used to find empirically the appropriate host strain that yields the lowest level of wild-type recombinants.

Alternative Strategies for Avoiding or Preventing the Immune Response Against Therapeutic Bacteriophages Lysis-defective bacteriophages of the invention encompass not only phage that have a defective lysin gene, but also phage that are defective in the lysis machinery due to defects other than in the Lys gene or in addition to the Lys gene. For example, rather than being defective in only the lysin gene, both the lysin gene and the holin gene can be deleted or altered to be non-functional in the phage and the lysis system. Such defective phage can be produced by expressing the missing or defective lysis system components on a helper plasmid in the bacterial host. Martin et al (J. Bacteriol. 180, 210 (1998) have shown that concomitant expression of both holin and lysin of the Pneumococcal phage Cp-1 in E. coli resulted in cell lysis. Similar strategies discussed above can be used to avoid generation of wild-type phage by recombination during the production phase.

Since the holins are the membrane-spanning proteins that allow phage lysins to access the bacterial cell wall murein, deletion or inactivation of the holin gene alone is also sufficient for generating therapeutic bacteriophages lacking immune response potential. Depending on the structure and properties of the specific phage, deletion or inactivation of either the lysin gene, the holin gene, or both could be employed to generate the desired therapeutic phage.

Any phage strain capable of facilitating direct or indirect harm to a bacteria (or other pathogen) (e.g., in inhibiting or interfering with transcription and/or translation of bacterial DNA (e.g., through competition of phage DNA for the same host cell machinery), inhibiting bacterial replication, and the like) is contemplated as useful in the present invention.

would be useful in combination with Lys minus bacteriophage for treating bacterial infections. Examples of suitable antimicrobial agents and the bacterial infections which can be treated with the specified antimicrobial agents are listed below. However, the present invention is not limited to the antimicrobial agents listed below as one skilled in the art could easily determine other antimicrobial agents useful in combination with Lys minus bacteriophage.

| Pathogen | Antimicrobial or antimicrobial group |
|---|---|
| *E. coli* (uncomplicated urinary tract infection) | trimethoprim-sulfamethoxazole (abbrev. TMO-SMO), or ampicillin; 1st generation cephalosporins, ciprofloxacin |
| *E. coli* systemic infection | ampicillin, or a 3rd generation cephalosporin; aminoglycosides, aztreonam, or a penicillin + a pencillinase inhibitor |
| *Klebsiella pneumoniae* | 1st generation cephalosporins; 3rd generation cephalosporins, cefotaxime, moxalactam, amikacin, chloramphenicol |
| Shigella (various) | ciprofloxacin; TMO-SMO, ampicillin, chloramphenicol |
| *Salmonella typhi* | chloramphenicol; ampicillin or TMO-SMO |
| *Salmonella* non-typhi species | ampicillin; chloramphenicol, TMO-SMO, ciprofloxacin |
| *Yersinia pestis* | streptomycin; tetracycline, chloramphenicol |
| *Enterobacter cloacae* | 3rd generation cephalosporins, gentamicin, or tobramycin; carbenicillin, amikacin, aztreonam, imipenem |
| *Haemophilus influenzae* - meningitis | chloramphenicol or 3rd generation cephalosporins; ampicillin |
| *Haemophilus influenzae* - other *H. influenza* infections | ampicillin; TMO-SMO, cefaclor, cefuroxime, ciprofloxacin |
| *Mycobacterium tuberculosis* and *M. avium-intracellulare* | isoniazid (INH) + rifampin or rifabutin, the above given along with pyrazinamide +/or ethambutol |
| *Neisseria meningitides* | penicillin G; chloramphenicol, or a sulfonamide |
| *Neisseria gonorrhoeae:* penicillin-sensitive | penicillin G; spectinomycin, ceftriaxone |
| *Neisseria gonorrhoeae:* penicillin-resistant | ceftriaxone; spectinomycin, cefuroxime or cefoxitin, ciprofloxacin |
| *Pseudomonas aeruginosa* | tobramycin or gentamycin (+/− carbenicillin, aminoglycosides; amikacin, ceftazidime, aztreonam, imipenem |
| *Staphylococcus aureus:* non-penicillinase-producing | penicillin G; 1st generation cephalosporins, vancomycin, imipenem, erythromycin |
| *Staphylococcus aureus:* penicillinase-producing | a penicillinase-resisting penicillin; 1st generation cephalosporins, vancomycin, imipenem, erythromycin |
| *Streptococcus pneumoniae* | penicillin G; 1st generation cephalosporins, erythromycin, chloramphenicol |
| *Vibrio cholera* | tetracycline; TMO-SMO |

Thus, phages that are lytic, and phages that are lysogenic but can later become lytic, can be adapted for use in the present invention.

Bacterial Infections Amenable to Bacteriophage Therapy

Any of a variety of bacterial infections can be treated using a therapeutic bacteriophage according to the invention. The bacterial infection may be localized (e.g., contained within an organ, at a site of a surgical wound or other wound, within an abscess), or may be systemic (e.g., the subject is bacteremic, e.g., suffers from sepsis).

The subject to be treated by the methods of the present invention include but are not limited to man, his domestic pets, livestock, fish, and the animals in zoos and aquatic parks (such as whales and dolphins).

The genetically modified Lys minus bacteriophage of the present invention can be used as a stand-alone therapy or as an adjunctive therapy for the treatment of bacterial infections. Numerous antimicrobial agents (including antibiotics and chemotherapeutic agents) are known in the art which Bacteriophage(s) suitable for use in treatment of a subject can be selected based upon the suspected bacterial pathogen infecting the subject. Methods for diagnosis of bacterial infections are well known in the art. Where such diagnosis involves culturing a biological sample from the subject, the clinician can at the same time test the susceptibility of the infecting pathogen to growth inhibition by one or more therapeutic phages that are candidates for subsequent therapy.

Bacteriophage of the invention can be first evaluated for rendering the target bacteria bacteriostatic in an appropriate in vitro or in vivo model of infection, e.g., a non-human animal model of infection, e.g., infection models using rodents (e.g., mice rats, hamsters, and the like), lagomorphs, canine, bovine, and the like. Suitable in vitro and in vivo infection models, as well as selection of such models that are appropriate, are well known in the art.

Efficacy of the bacteriophage therapy according to the invention can be monitored according to methods well known in the art. In general, successful treatment is that which results in inhibition of bacterial growth so as to allow the immune system of the infected host to facilitate clearance of the infecting bacteria, thereby reducing the bacterial load in the host.

In addition to their therapeutic uses in vivo, the bacteriophage of the invention can also be used to generate an incapacitated whole cell bacterial immunogenic composition, which may be used as, for example, a vaccine, as described in commonly owned U.S. provisional application Ser. No. 60/325,796 entitled "Incapacitated Whole-Cell Bacterial Vaccines", filed on Sep. 27, 2001, and as described in commonly owned co-pending U.S. application entitled "Incapacitated Whole-Cell Bacterial Immunogenic Compositions", filed on the same date herewith and claiming priority to the above-mentioned provisional application, Attorney Docket No. GANG-002. By "incapacitated" is meant that the bacterial cell is in a state of irreversible bacteriostasis. While the bacterium retains its structure—and thus retains the immunogenicity, antigenicity, and receptor-ligand interactions associated with a wild-type bacterium—it is not capable of replicating due to the presence of an infecting phage with in the bacterial cell. Such vaccines are useful in eliciting a prophylactic or therapeutic immune response against the bacterial pathogen from which the vaccine is made.

Formulations, Routes of Administration and Dosages

The bacteriophage of the invention can be formulated in any manner suitable which provides for delivery of the bacteriophage to the site of infection, and which maintains the ability of the phage to infect and inhibit replication of the bacterial host cell.

Formulations and Pharmaceutical Compositions

The invention further contemplates pharmaceutical compositions comprising at least one bacteriophage of the invention provided in a pharmaceutically acceptable excipient. The formulations and pharmaceutical compositions of the invention thus contemplate formulations comprising an isolated bacteriophage specific for a bacterial host; a mixture of two, three, five, ten, or twenty or more bacteriophage that infect the same bacterial host; and a mixture of two, three, five, ten, or twenty or more bacteriophage that infect different bacterial hosts or different strains of the same bacterial host. (e.g., a mixture of bacteriophage that collectively infect and inhibit the growth of multiple strains of Staphylococcus aureus). In this manner, the compositions of the invention can be tailored to the needs of the patient.

Various pharmaceutically acceptable excipients are well known in the art. As used herein, "pharmaceutically acceptable excipient" includes any material which, when combined with an active ingredient of a composition, allows the ingredient to retain biological activity and without causing disruptive reactions with the subject's immune system.

Exemplary pharmaceutically carriers include sterile aqueous of non-aqueous solutions, suspensions, and emulsions. Examples include, but are not limited to, any of the standard pharmaceutical excipients such as a phosphate buffered saline solution, water, emulsions such as oil/water emulsion, and various types of wetting agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

A composition comprising a bacteriophage of the invention may also be lyophilized using means well known in the art, for subsequent reconstitution and use according to the invention.

Also of interest are formulations for liposomal delivery, and formulations comprising microencapsulated bacteriophage. Compositions comprising such excipients are formulated by well known conventional methods (see, for example, Remington's Pharmaceutical Sciences, Chapter 43, 14th Ed., Mack Publishing Col, Easton Pa. 18042, USA).

In general, the pharmaceutical compositions can be prepared in various forms, such as granules, tablets, pills, suppositories, capsules (e.g. adapted for oral delivery), microbeads, microspheres, liposomes, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value.

The pharmaceutical composition can comprise other components in addition to the bacteriophage. In addition, the pharmaceutical compositions may comprise more than one bacteriophage, for example, two or more, three or more, five or more, or ten or more different bacteriophage, where the different bacteriophage may be specific for the same or different bacteria. For example, the pharmaceutical composition can contain multiple (e.g., at least two or more) defined Lys minus bacteriophage, wherein are least two of the phage in the composition have different bacterial host specificity. In this manner, the Lys minus bacteriophage composition can be adapted for treating a mixed infection of different bacteria, e.g., by selecting different groups of bacteriophage of differing specificity so as to contain at least one bacteriophage for each bacteria (e.g., strain, species, etc.) suspected of being present in the infection (e.g, in the infected site). As noted above, the bacteriophage can be administered in conjunction with other agents, such as a conventional antimicrobial agent (see table above). In some embodiments, it may be desirable to administer the bacteriophage and antibiotic within the same formulation.

Routes of Administration and Dosages

The route of administration and dosage will vary with the infecting bacteria, the site and extent of infection (e.g., local or systemic), and the subject being treated. The routes of administration include but are not limited to: oral, aerosol or other device for delivery to the lungs, nasal spray, intravenous (IV), intramuscular, intraperitoneal, intrathecal, vaginal, rectal, topical, lumbar puncture, intrathecal, and direct application to the brain and/or meninges. Excipients which can be used as a vehicle for the delivery of the phage will be apparent to those skilled in the art. For example, the free phage could be in lyophilized form and be dissolved just prior to administration by IV injection. The dosage of administration is contemplated to be in the range of about 1 million to about 10 trillion/per kg/per day, and preferably about 1 trillion/per kg/per day, and may be from about $10^6$ pfu/kg/day to about $10^{13}$ pfu/kg/day.

The phage are administered until successful elimination of the pathogenic bacteria is achieved. Thus the invention contemplates single dosage forms, as well as multiple dosage forms of the compositions of the invention, as well as methods for accomplishing delivery of such single and multi-dosages forms.

With respect to the aerosol administration to the lungs, the modified Lys minus phage is incorporated into an aerosol formulation specifically designed for administration to the lungs by inhalation. Many such aerosols are known in the art, and the present invention is not limited to any particular formulation.

EXAMPLES

The foregoing embodiments of the present invention are further described in the following Examples. However, the present invention is not limited by the Examples, and variations will be apparent to those skilled in the art without departing from the scope of the present invention. In particular, any bacteria and phage known to infect said bacteria can be substituted in the experiments of the following examples. The following examples are put forth so as to provide those of ordinary skill in the art with a complete disclosure and description of how to make and use the present invention, and are not intended to limit the scope of what the inventors regard as their invention. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Creation of Lys Minus T4 Phage

The nucleotide sequence of the lysozyme (e) gene of bacteriophage T4 together with 130 additional nucleotides on each side was reported by Owen et al (J. Mol. Biol. 165, 229, 1983). The DNAs corresponding to 100 nucleotides of the upstream and downstream regions of the e gene are isolated by PCR and cloned into the ampicillin-resistant plasmid pUC 18 with unique restriction sites (Xba I and Pst I) between the two regions ((Sambrook, J. et al Molecular Cloning: A Laboratory Manual, $2^{nd}$ ed. Cold Spring Harbor Laboratory Press, Cold Spring Harbor, N.Y.). A DNA cassette containing the gene for a mutant form of the green fluorescent protein (GFP) which fluoresces 40-fold more brightly than the wild type protein, is generated as an Xba 1-Pst I fragment from plasmid pmut2 carrying gfp (Cormack, B. P., Valdivia, R. H. and Falkow, S. Gene 173, 33, 1996) and introduced between the upstream and downstream sequences of the lysozyme gene in pUC18(pGG8). The promoter and terminator for the expression of GFP in this cassette are replaced by the early promoter of the T4 dihydrofolate reductase gene frd (Rosenberg, M. and Court, D. Ann. Rev. Genet. 13, 319, 1979) at the 5' end and the transcription terminator situated between genes 44 and 45 of T4 (Spicer and Konigsberg in Bacteriophage T4 eds. Mathews, Kutter, Mosig and Berget, American Society for Microbiology, Washington, D.C., 1983, pp. 299) at the 3' end, respectively. The frd promoter is in the immediate early class of T4 promoters that are among the first to be expressed in bacterial cells infected with T4. The host RNA polymerase is used for transcription from this promoter.

This plasmid pGG8 is transformed into E. coli HB101 cells by the RbCl method and selected for ampicillin resistance. E. coli HB101 cells harboring the plasmid pGG8 with the mutant lysozyme gene is then infected with wild-type T4 phage at a low multiplicity of infection. During replication, some of it recombines with the mutant lysozyme gene carried on the plasmids in the cells to yield Lys minus phage. It is likely that recombination in any cell will not be 100% efficient. Both types of phages are collected by lysing the bacterial cells with chloroform, and the Lys minus phage is separated from the wild-type by plaque purification. Each plaque is then tested to see if it is wild-type or Lys minus. Lys minus phages can be identified by the green fluorescence of replica plates under UV since GFP is expressed under the T4 early promoter. This can be further confirmed by testing the phage from each plaque on normal E. coli HB101 as well as cells expressing the lysin gene described below. Whereas wild-type phage kills both hosts, Lys minus phage kills only the host cells expressing lysin.

Example 2

Production of Lys Minus T4 Phase in E. coli

The two-gene lysis system of the Pneumococcal phage Cp-1 has been cloned and expressed in E. coli (Martinet al. J. Bacteriol. 180, 210 (1998). PCR using Cp-1 DNA as the template generates DNA fragments containing the cpl1 (lysin) gene or the cassette cph1-cpl1 (holin-lysin) genes, in which the genes retain their own ribosome-binding sites. Using appropriate oligonucleotides, Sac II and Sac I restriction sites are created at the 5' and 3' ends of the PCR fragments for cloning into plasmid pNM185 (Mermod et al. J. Bacteriol. 167, 447 (1986)). The cpl1 gene or the cassette containing cph1 and cpl1 genes are expressed under the control of a positively regulated promoter (Pm) of the meta pathway operon of the TOL plasmid. Transcription of the genes from Pm is specifically induced by the product of the xylS regulator gene only when effector molecules like 3-methyl benzoate are present. Transformation of E. coli HB101 cells with the pNM185 plasmids carrying the cpl1 or cph1-cpl1 cassette is carried out by the RbCl method ((Sambrook et al. Molecular Cloning: A Laboratory Manual, $2^{nd}$ ed. Cold Spring Harbor Laboratory, Cold Spring Harbor, N.Y. (1989)). The transformed E. Coli. HB101 cells are grown in LB broth or other suitable medium and inoculated with the Lys minus T4 phage. At the appropriate time, the expression of cpl1 or the cph1-cpl1 cassette on the pNM185 plasmid is induced by the addition of 2 mM 3-methyl benzoate to effect release of the Lys minus T4 phage progeny.

Example 3

Creation of Plasmid pGMB021 for use in Lys Minus Recombinant Phase Generation

Materials and Methods. Tag DNA polymerase, dNTP's, Calf Intestinal Phosphatase, Restriction enzymes, primers and T4 DNA ligase were procured from Bangalore Genei Pvt. Ltd (BGPL), Bangalore. pRSET vectors were from Invitrogen Ltd, USA.

The ligations were performed with vector:insert ratio of 1:10 M. The PCR products along with digested vectors were purified from agarose gel using Qiagen gel extraction kit reagents unless mentioned otherwise.

Construction of T4 lysozyme clone in T7promoter based pRSETB vector (pRSETB-T4L). PCR amplification of the lysin gene of T4 was performed with the wild type T4 phage obtained from BGPL, using the following primers:

```
GMB1: Forward
                                   (SEQ ID NO:1)
5'CG GAA TTC CAT ATG AAT ATA TTT GAA ATG
TTA CGT 3'

GMB2: Reverse
                                   (SEQ ID NO:2)
5' AA AGC GGC CGC AAG CTT TAG ATT TTT ATA CGC GTC
CCA 3'
```

Initial denaturation was at 95° C. for 4 min, followed by 30 cycles of denaturation at 95° C. for 30 sec, annealing at 55° C. for 30 sec, and extension at 72° C. for 30 sec. The contents were finally extended for 7 min at 72° C.

Next, the PCR product obtained was purified and klenow filled in before ligation to pRSETB vector digested with PvuII and dephosphorylated with CIP. The vector to insert ratio was maintained at 1:10M. The ligation was performed at 22° C. for 5 hours and then DH5 alpha competent cells were transformed with the above ligation mix. Transformants were then selected on LB amp plate (100 ug/ml final concentration) at 37° C. overnight. The transformants were screened by Pool colony PCR and the positive clones were then checked for restriction digestion after DNA isolation.

Figure 2:
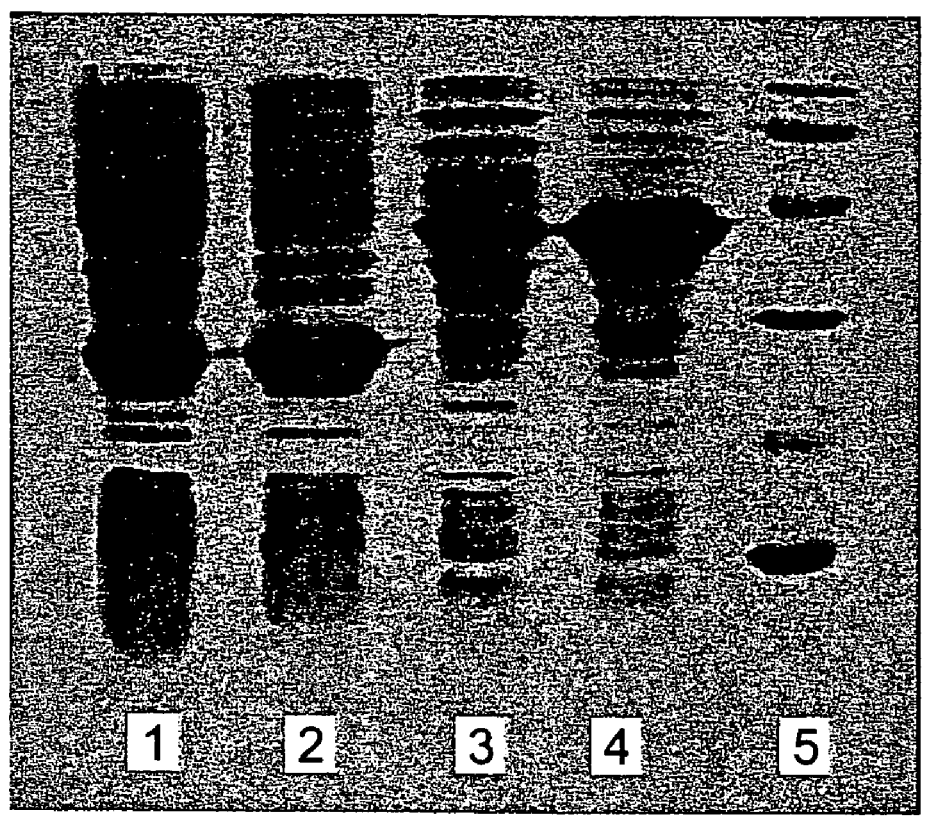
FIG. 2 illustrates SDS-PAGE of the gene products produced by plasmids pGMB011 and pGMB021 (Lane 1: pGMB011, Uninduced; Lane 2: pGMB011, Induced; Lane 3: pGMB021, Uninduced; Lane 4: pGMB021, Induced; Lane 5: 14–97 KDa marker).

The DNA of the positive clones was sequenced by ABI Prism of Pharmacia. The above clone expressed T4 lysozyme protein as seen on SDS-PAGE gel. The protein was a His tagged lysin protein of 25 KDa as expected (see FIG. 2, lanes 1 and 2). PGMB011 was selected for further use.

Construction of GFP as his tag fusion protein in pRSETA vector (pRSETA-GFP). To interrupt the lysin gene with a reporter gene, GFP gene was chosen. First, the GFP gene was amplified from pUC-GFP plasmid in the GFP teaching kit of BGPL, using the following primers:

```
GMB5: Forward
                                   (SEQ ID NO:3)
5' CC GGA ATT CAT ATG AGT AAA GGA GAA GAA CTT
TTC 3'
GMB6: Reverse
                                   (SEQ ID NO:4)
5' CC GGA ATT CAT TTA TTT GTA TAG TTC ATC CAT
GCC 3'
```

Initial denaturation was at 95° C. for 4 min, followed by 30 cycles of denaturation at 94 deg C. for 30 sec, annealing at 60° C. for 30 sec and extension at 72° C. for 30 sec. The final extension was at 72° C. for 7 min. The purified product was digested with EcoR1 and then ligated with pRSETA cut with EcoR1.

The clones were then screened by Pool colony PCR for GFP and small scale expression of GFP was seen on SDS-PAGE. All the clones were checked under UV light for the GFP fluorescence which indicated that the clone has GFP in the correct orientation with respect to the T7 promoter. The size of the GFP protein was 36 KDa as expected.

Interruption of the T4 lysin gene with GFP in frame with the 5' end of the T4 lysin gene to construct pGMB021. The GFP fragment from the pRSETA-GFP clone was then subcloned into partially digested pGMB011 (a pRSETB-T4L vector produced above) with EcoR1. The transformants were screened for PCR with GMB5/GMB6 and then checked by small scale expression of the his-tagged lysin-GFP fusion protein. The His-tagged lysin-GFP fusion protein expressed from the above clone (42 KDa) (see FIG. 2, lanes 3 and 4) and it showed fluorescence under UV indicating that the GFP gene was intact in this construct.

Figure 3:
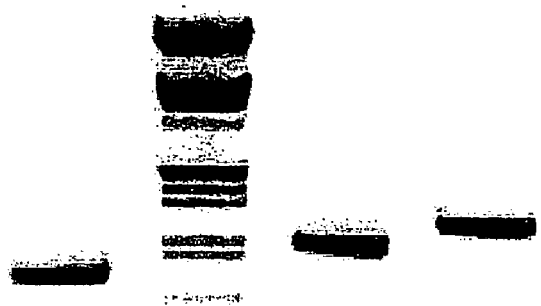
FIG. 3 is a photograph illustrating the results of PCR of the pGMB021 construct used for recombination experiments (Lane 1: GMB1/GMB2 primers; Lane 2: GMB2/GMB5 primers; Lane 3: marker; Lane 4: GMB5/GMB6 primers).

The above clone was further tested for PCR with GMB1/GMB2 primers (T4 lysin specific primers). As expected the PCR with GMB1/GMB2 gave a product of lysine-GFP-lysin of approximately 1200 bp showing the intactness of lysin and GFP genes (FIG. 3). This clone was used in the recombination experiment described in Example 4 below.

Example 4

Generation and Isolation of Lys Minus Recombinant Phase

DH5α cells containing the plasmid pGMB021 (which contains the defective lysin gene with the GFP insertion) were infected with wild type T4 phage at 2.5 m.o.i. This high multiplicity of infection ensures that every cell is infected with at least one phage. Infection of the pGMB021-DH5α cells results in production of lysin-deficient phage as described in Example 3 above. After 40 minutes of incubation, chloroform (1%) was added and the lysate centrifuged. The supernatant was separated and aerated for 30 minutes at room temperature for evaporation of the residual chloroform.

The lysate was treated with DNase (50 ug/ml) for 30 min at 37° C. to digest the chromosomal and plasmid DNA, and then was titred. Next, normal *E. coli* cells (bearing no plasmid) were infected with the lysate at 0.1 m.o.i. This low multiplicity of infection ensures that all the infected cells contain a single phage, which in turn serves to separate the lysin-deficient phage and the wild type phages.

The above infection mix was incubated at 37° C. for 30 min and then centrifuged. The cell pellet and supernatant were separated. The cells containing the recombinant Lys minus phage will not lyse and were therefore be present in the cell pellet among uninfected cells. The supernatant was discarded, as this fraction was likely to contain most of the wild type phages. The pellet was then resuspended in culture medium (Luria Broth) and lysed with egg-white lysozyme (10 ug/ml) and chloroform (2%). This lysate was used to infect BL21(DE3) pLys E cells at 0.1 m.o.i. and plated on a lawn of the same cells. These cells were specifically chosen for this step since they constitutively express, from a plasmid, T7 phage lysozyme and would aid Lys minus phages to form plaques.

Two types of plaques were seen on the plate—several wild type plaques and a few minute or pin-point plaques. The pin-point plaques were picked and resuspended in culture medium. Next, these were allowed to infect BL21 (DE3) pLysE cells and then plated on a 1:1 mixture of BL21 (DE3) pLysE (which make T7 lysozyme) and LE392 cells (no lysozyme).

Figure 4:
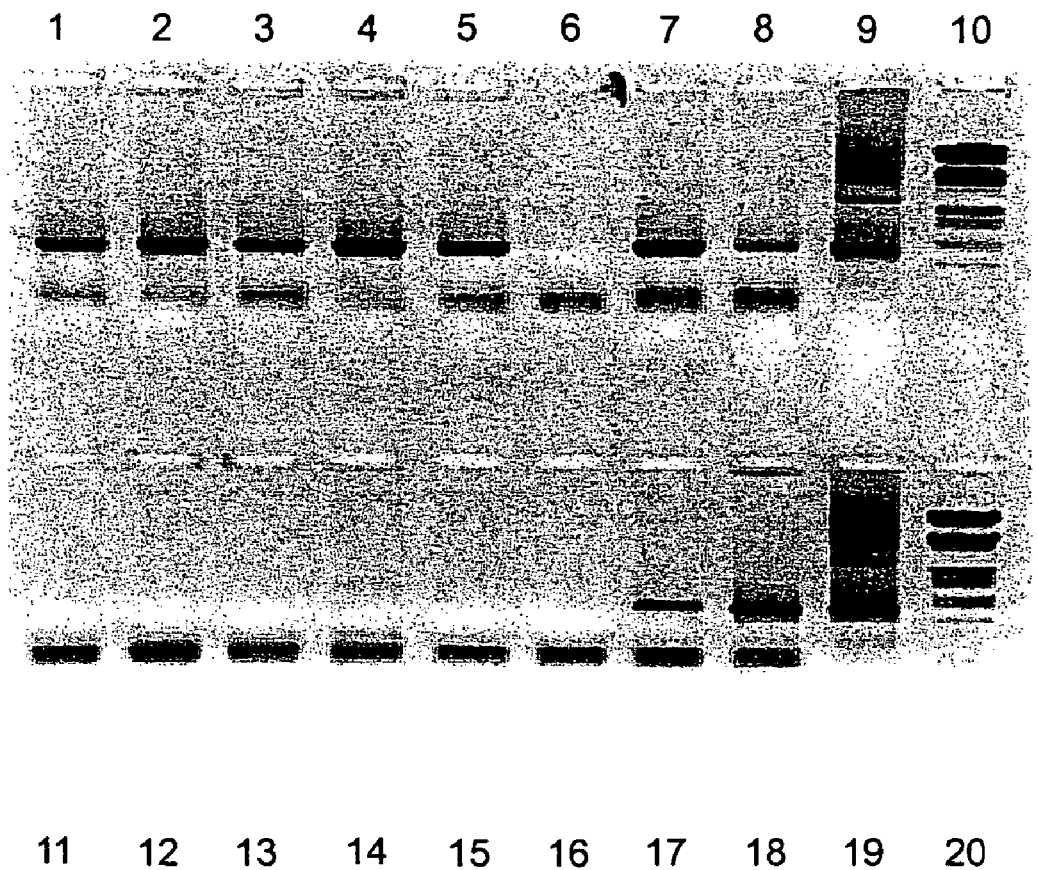
FIG. 4 is a photograph illustrating the results of PCR of turbid plaques for GFP gene product (Lanes 1–5,7,8,17 & 18: pools positive for GFP gene product; Lanes 6, 11–16: pools negative for GFP gene product; Lanes 9, 19: positive control; Lanes 10, 20: MW marker).

Turbid areas representing the recombinant phage were distinguishable among wild type plaques on the lawn of the mixture of cells. These turbid areas were picked up. Part were resuspended in water for PCR and the remaining were resuspended in culture medium. GFP gene product was amplifiable from many of the turbid plaques (FIG. 4).

Figure 5:
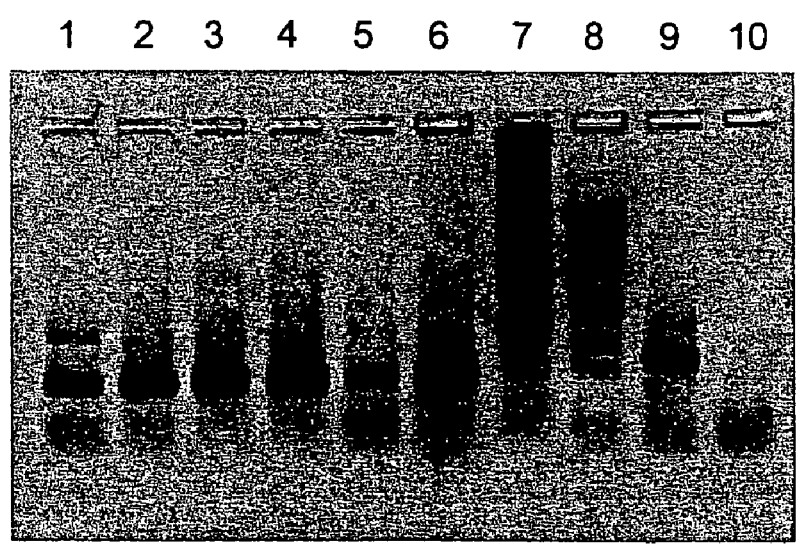
FIG. 5 is a photograph illustrating the results of PCR of turbid plaques for Lysin-GFP-Lysin gene product (Lanes 1–6: turbid plaques #1, 2, 3, 4, 7, 8; Lane 7: positive control for Lysin-GFP-Lysin product (plasmid DNA); Lane 8: MW marker; Lane 9: positive control for lysin product (plasmid DNA); Lane 10: negative control).
Figure 6:
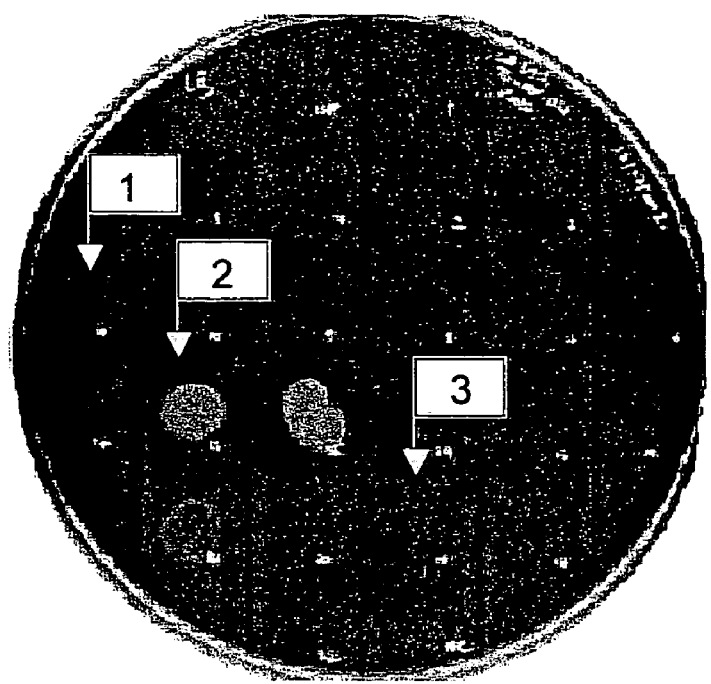
FIG. 6 illustrates recombinant phage lysates spotted on a lawn of E. coli showing different levels of contamination with wild type phage or total absence of wild plaques (Spot #1: lysate #11 which shows a countable number of wild plaques; Spot #2: lysate which shows high number of wild plaques which completely lysed the cells; Spot #3: lysate which does not show any wild plaques).
Figure 7:
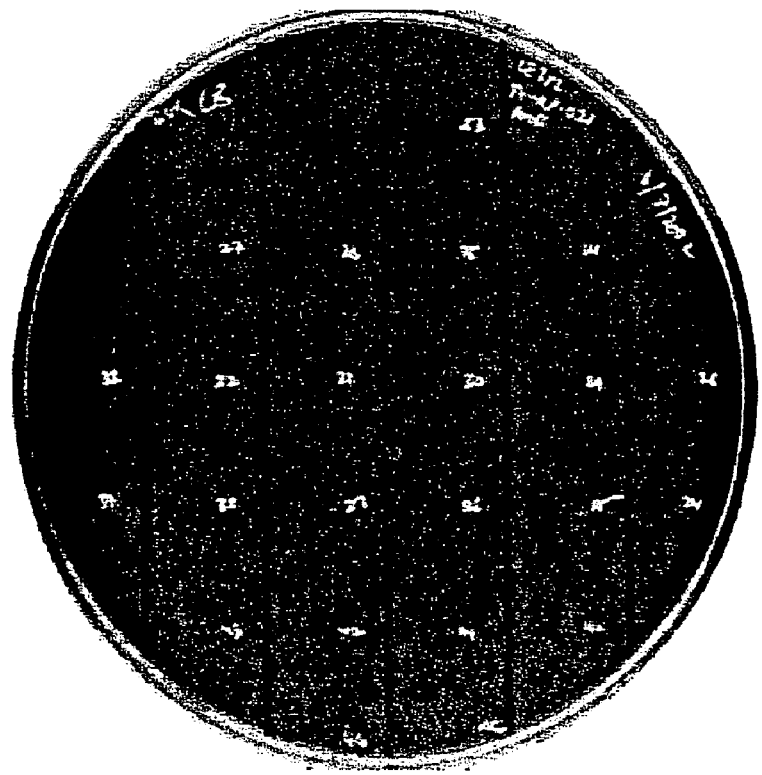
FIG. 7 illustrates recombinant phage containing lysates spotted on a lawn of E. coli showing absence of plaques.

The full length T4 lysin-GFP-lysin was also amplified. However, the wild type lysin gene product was also present, indicating presence of wild type phage (FIGS. 5 and 6). Selective elimination of wild type phage form these lysates were done by infecting cells at low m.o.i and lysis of the cells at 40 min. At this time, the wild type phage would have entered another round of infection and will be in the eclipse stage (in DNA form). Lysis of cells thus destroys the wild type phage before assembly into particles. After 3–5 rounds of such elimination, the lysates were plaque-less (FIG. 7).

Figure 8:
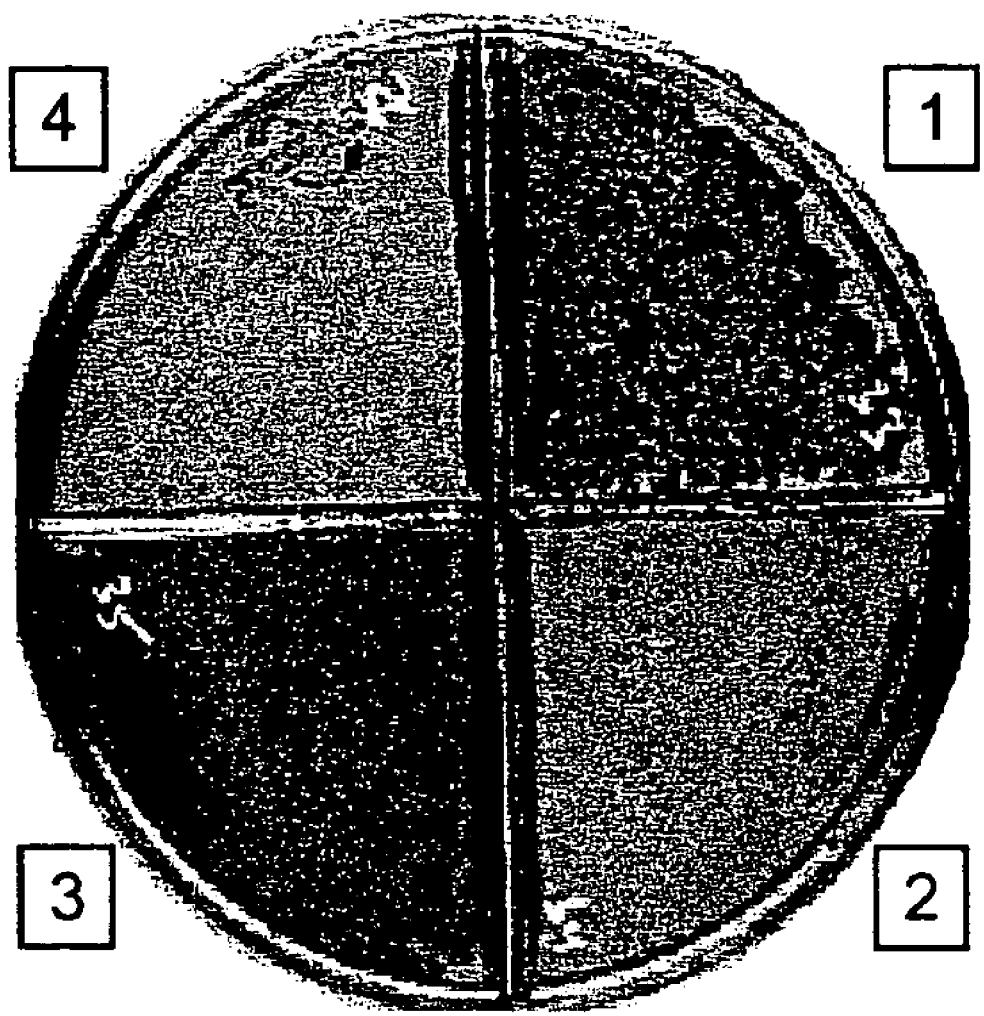
FIG. 8 illustrates recombinant phage (RP)-containing lysates leading to loss of viability of E. coli cells infected (Quadrant #1:~50% loss of viability seen with RP-lysate #33; Quadrants #2 & 4: total loss of viability in case of RP-lysates #34 & #36; Quadrant #3: no significant loss of viability with RP-lysate #35).

Confirmation of the presence of the recombinant Lys minus phage in such lysates and quantitation was done by estimating the number of viable cells after infection. Loss of viability of infected cells was evident upon plating the infection mix (FIG. 8).

In order to enrich the recombinant Lys minus phage and avoid the use of chloroform and external supplementation of lysozyme, a temperature sensitive mutant *E. coli* cell type (RE 7) (which grows at 30° C. and lyses at 42° C.) was used. Enrichment of the recombinant Lys minus phage to a level of about $2 \times 10^8$/ml was attained. This preparation is evaluated for efficacy in eliminating *E. coli* infection in an mouse model of infection available in the art.

That which is claimed is:

1. A method for inhibiting growth of bacteria in an infected subject, the method comprising:
   administering to the infected subject a lysis-defective bacteriophage that can infect an infecting bacteria present in the infected subject, wherein the bacteriophage is administered in an amount effective to inhibit growth of the infecting bacteria.

2. The method of claim 1, wherein the infecting bacteria are drug resistant bacteria.

3. The method of claim 1, wherein the bacterial infection is at a local site.

4. The method of claim 1, wherein at least two or more different lysis-defective bacteriophage are administered to the subject.

5. The method of claim 4, wherein at least two of the lysis-defective bacteriophage have specificity for different bacterial host cells.

6. The method of claim 5, wherein the subject has a mixed bacterial infection.

7. The method of claim 1, wherein the infecting bacteria is of a genus selected from the group consisting of *Mycobacteria, Staphylococci, Vibrio, Enterobacter, Enterococcus, Escherichia, Haemophilus, Neisseria, Pseudomonas, Shigella, Serratia, Salmonella, Streptococcus, Klebsiella* and *Yersinia*.

8. The method of claim 1, wherein said lysis-defective bacteriophage is a lys minus bacteriophage.

9. A method for treating a bacterial infection in an infected subject, the method comprising:
   administering to the infected subject a lysis-defective bacteriophage that can infect an infecting bacteria present in the infected subject, wherein the bacteriophage is administered in an amount effective to inhibit replication of the infecting bacteria;
   wherein bacterial load is reduced in the infected subject and the bacterial infection is treated.

10. The method of claim 9, wherein the infecting bacteria are drug resistant bacteria.

11. The method of claim 9, wherein the bacterial infection is systemic.

12. The method of claim 9, wherein the bacterial infection is at a local site.

13. The method of claim 9, wherein the subject has a bacterial infection at a local site.

14. The method of claim 13, wherein said administering is to the local site of infection.

15. The method of claim 9, wherein at least two or more different lysis-defective bacteriophage are administered to the subject.

16. The method of claim 15, wherein at least two of the lysis-defective bacteriophage have specificity for different bacterial host cells.

17. The method of claim 9, wherein the subject has a mixed bacterial infection.

18. The method of claim 9, wherein the infecting bacteria is of a genus selected from the group consisting of *Mycobacteria, Staphylococci, Vibrio, Enterobacter, Enterococcus, Escherichia, Haemophilus, Neisseria, Pseudomonas, Shigella, Serratia, Salmonella, Streptococcus, Klebsiella* and *Yersinia*.

19. The method of claim 9, wherein said lysis-defective bacteriophage is a lys minus bacteriophage.

20. A pharmaceutical composition comprising a lysis-defective bacteriophage present in an amount effective to inhibit growth of bacterium in an infected subject and a pharmaceutically acceptable carrier, where upon contacting a bacterial host cell, the lysis-defective bacteriophage effects inhibition of growth of the bacterial host cell in the infected subject.

21. The composition of claim 20, wherein the bacteriophage is in lyophilized form.

22. The composition of claim 20, wherein said composition comprises a mixture of two or more lysis-defective bacteriophage.

23. The composition of claim 20, wherein said composition comprises a mixture of two or more different lysis-defective bacteriophage that effect inhibition of at least two different bacterial hosts.

24. The pharmaceutical composition of claim 20, wherein said lysis-defective bacteriophage is a Lys minus bacteriophage.

25. A method for treating a bacterial infection in an infected subject with a therapeutic bacteriophage so as to provide for reduced bacteriophage clearance by the subject's immune system, the method comprising:
   administering to the subject a lysis-defective bacteriophage that can infect an infecting bacteria present in the subject, wherein the lysis-defective bacteriophage is administered in an amount effective to provide for inhibition of replication of the infecting bacteria;
   wherein the lysis-defective bacteriophage does not cause significant lysis of the infecting bacteria, thereby reducing the number of bacteriophage exposed to an immune response by the subject and providing for reduced clearance of the bacteriophage relative to that associated with a wild-type bacteriophage.

26. The method of claim 25, wherein the subject has a bacterial infection at a local site.

27. The method of claim 26, wherein said administering is to the local site of infection.

28. The method of claim 25, wherein at least two or more different lysis-defective bacteriophage are administered to the subject.

29. The method of claim 28, wherein at least two of the lysis-defective bacteriophage have specificity for different bacterial host cells.

30. The method of claim 29, wherein the subject has a mixed bacterial infection.

31. The method of claim 25, wherein said lysis-defective bacteriophage is a Lys minus bacteriophage.

32. An isolated lysis-defective bacteriophage, which bacteriophage is defective in production of a functional lysin or holin protein, wherein the lysis-defective bacteriophage is capable of infecting a bacterial host cell and inhibiting replication by the infected host cell without causing significant lysis of the host cell by virtue of the action of bacteriophage lysis system.

33. The isolated lysis-defective bacteriophage of claim 32, wherein said bacteriophage is a Lys minus bacteriophage.

* * * * *

SEQUENCE LISTING

```
<160> NUMBER OF SEQ ID NOS: 4

<210> SEQ ID NO 1
<211> LENGTH: 35
<212> TYPE: DNA
<213> ORGANISM: Artificial Sequence
<220> FEATURE:
<223> OTHER INFORMATION: primer

<400> SEQUENCE: 1
cggaattcca tatgaatata tttgaaatgt tacgt                              35

<210> SEQ ID NO 2
<211> LENGTH: 38
<212> TYPE: DNA
<213> ORGANISM: Artificial Sequence
<220> FEATURE:
<223> OTHER INFORMATION: primer

<400> SEQUENCE: 2
aaagcggccg caagctttag atttttatac gcgtccca                           38

<210> SEQ ID NO 3
<211> LENGTH: 35
<212> TYPE: DNA
<213> ORGANISM: Artificial Sequence
<220> FEATURE:
<223> OTHER INFORMATION: primer

<400> SEQUENCE: 3
ccggaattca tatgagtaaa ggagaagaac ttttc                              35

<210> SEQ ID NO 4
<211> LENGTH: 35
<212> TYPE: DNA
<213> ORGANISM: Artificial Sequence
<220> FEATURE:
<223> OTHER INFORMATION: primer

<400> SEQUENCE: 4
ccggaattca tttatttgta tagttcatcc atgcc                              35
```